United States Patent
Sakaguchi et al.

(10) Patent No.: US 10,285,721 B2
(45) Date of Patent: May 14, 2019

(54) MEDICAL MANIPULATOR

(71) Applicant: Karl Storz SE & Co. KG, Tuttlingen (DE)

(72) Inventors: Yuuki Sakaguchi, Fujinomiya (JP); Shinji Ishida, Fujinomiya (JP)

(73) Assignee: Karl Storz SE & Co. KG, Tuttlingen (DE)

( * ) Notice: Subject to any disclaimer, the term of this patent is extended or adjusted under 35 U.S.C. 154(b) by 360 days.

(21) Appl. No.: 14/871,279

(22) Filed: Sep. 30, 2015

(65) Prior Publication Data

US 2016/0015409 A1 Jan. 21, 2016

Related U.S. Application Data

(63) Continuation of application No. PCT/JP2013/060014, filed on Apr. 1, 2013.

(51) Int. Cl.
*A61B 17/29* (2006.01)
*A61B 18/14* (2006.01)
(Continued)

(52) U.S. Cl.
CPC .......... *A61B 17/29* (2013.01); *A61B 18/1445* (2013.01); *F16D 1/10* (2013.01);
(Continued)

(58) Field of Classification Search
CPC ..... A61B 17/29; A61B 17/28; A61B 17/2909; A61B 2017/00199; A61B 2017/003;
(Continued)

(56) References Cited

U.S. PATENT DOCUMENTS 3,835,858 A * 9/1974 Hagen ................ A61B 17/1633
408/141
4,685,823 A * 8/1987 Lopez ....................... F16D 1/06
29/558

(Continued)

FOREIGN PATENT DOCUMENTS

JP 2004278751 A 10/2004
JP 2004305590 A 11/2004
(Continued)

OTHER PUBLICATIONS

International Search Report Application No. PCT/JP2013/060014 Completed: Apr. 22, 2013; dated May 14, 2013 2 pages.
(Continued)

*Primary Examiner* — Michael F Peffley
(74) *Attorney, Agent, or Firm* — WHITMYER IP GROUP LLC

(57) ABSTRACT

A medical manipulator wherein a first section provided with a driven coupling is detachably attached to a second section provided with a driving coupling that includes a drive source and is driven by the drive source. The driving coupling and the driven coupling are fitted to each other to transmit the drive force from the drive source to a tip-end operation part. In at least one coupling among the driving coupling and the driven coupling, tooth ends on the side where the fitting of the driving coupling and the driven coupling begins when the first section and the second section are connected become thinner towards the axial-direction end surface.

12 Claims, 23 Drawing Sheets

(51) Int. Cl.
  *F16D 1/10* (2006.01)
  *F16D 1/108* (2006.01)
  *A61B 17/00* (2006.01)
  *A61B 18/00* (2006.01)
  *F16D 11/00* (2006.01)

(52) U.S. Cl.
  CPC .............. *F16D 1/101* (2013.01); *F16D 1/108* (2013.01); *A61B 2017/003* (2013.01); *A61B 2017/0046* (2013.01); *A61B 2017/00199* (2013.01); *A61B 2017/00314* (2013.01); *A61B 2017/00398* (2013.01); *A61B 2017/00477* (2013.01); *A61B 2017/2903* (2013.01); *A61B 2017/2927* (2013.01); *A61B 2018/00178* (2013.01); *F16D 2001/103* (2013.01); *F16D 2011/008* (2013.01)

(58) Field of Classification Search
  CPC .......... A61B 2017/00314; A61B 2017/00398; A61B 2017/0046; A61B 2017/00477; A61B 2017/2903; A61B 2017/2927; A61B 2017/2901; A61B 2017/292; A61B 2017/00318; A61B 2017/00407; A61B 2017/00464
  See application file for complete search history.

(56) References Cited

U.S. PATENT DOCUMENTS

| | | | |
|---|---|---|---|
| 5,888,200 A | 3/1999 | Walen | |
| 5,941,891 A * | 8/1999 | Walen | A61B 17/1622 606/167 |
| 6,958,071 B2 * | 10/2005 | Carusillo | A61B 17/32002 606/170 |
| 8,419,760 B2 * | 4/2013 | Wiebe, III | A61B 17/1628 279/145 |
| 2001/0041911 A1 | 11/2001 | Dittrich et al. | |
| 2002/0085858 A1 | 7/2002 | Yamaguchi et al. | |
| 2004/0010258 A1 | 1/2004 | Carusillo et al. | |
| 2009/0171147 A1 | 7/2009 | Lee et al. | |
| 2009/0270899 A1 | 10/2009 | Carusillo et al. | |
| 2015/0297237 A1 * | 10/2015 | Hafner | A61B 17/1114 606/49 |

FOREIGN PATENT DOCUMENTS

JP 2004329624 A 11/2004
JP 2008104854 A 5/2008

OTHER PUBLICATIONS

European Search Report Application No. EP13881436 Completed: Sep. 15, 2016; dated Sep. 21, 2016 8 pages.

\* cited by examiner

MEDICAL MANIPULATOR

FIELD OF THE INVENTION

The present invention relates to a medical manipulator equipped with a drive source.

BACKGROUND OF THE INVENTION

In an endoscopic surgical operation (also referred to as "laparoscopic surgery"), one or a plurality of holes are punctured in the abdomen or the like of a patient, trocars (cylindrical instruments) are inserted through the holes, and a laparoscope (camera) and a plurality of forceps are inserted into the body cavity via the respective trocars. Grippers for gripping biological tissue, scissors, or blades of an electrosurgical scalpel are mounted to the distal end of the forceps as an end effector.

If the laparoscope and the forceps are inserted into the body cavity, an operator operates the forceps while viewing a state of the inner portion of the abdominal cavity, which is shown on a monitor that is connected to the laparoscope. Since the surgical procedure does not require a laparotomy, the burden on the patient is reduced, which reduces the number of days for postoperative recovery and leaving the hospital. For this reason, the fields that such an operative method can be applied to are expected to expand.

Other than typical forceps that are not provided with joints at distal end portions thereof, as forceps that are inserted through a trocar, forceps referred to as a medical manipulator have been developed that are provided with joints at distal end portions and which can carry out a rolling operation or a tilting operation of an end effector (for example, refer to Japanese Patent No. 4391762). In accordance with such a medical manipulator, a high degree of operational freedom is facilitated in the body cavity, manual procedures are made easy, and thus there are a large number of medical cases to which the medical manipulator may be applied.

Further, with the aim of improving operability and facilitating manipulation, a medical manipulator has been proposed that carries out a portion or all of the operations of a distal end working unit by a drive source (motor) (see, for example, Japanese Laid-Open Patent Publication No. 2008-104854). With this type of medical manipulator, a motor serving as a drive source is mounted in a handle on which an operating button is provided. An operating member (a portion corresponding to a forceps) including a shaft and the distal end working unit is capable of being attached and detached with respect to the handle. Multiple types of implements, such as a needle driver, an electrosurgical scalpel, and the like may be used as operating members, and various different types of such operating members are selectively attachable and detachable to and from the handle.

SUMMARY OF THE INVENTION

Incidentally, in the case that a portion on which the distal end working unit is disposed and a portion on which the drive source is disposed are capable of attachment and detachment to and from each other, as in the above-described medical manipulator, for transmitting a driving force from the drive source to the distal end working unit, it can be considered to adopt a configuration in which, accompanying connection of the two portions, the drive coupling and the driven coupling are fitted together mutually, wherein one of the couplings is a male coupling and the other of the couplings is a female coupling. However, when the drive coupling and the driven coupling contact one another, in the event that the teeth thereof are overlapped, it becomes difficult for the drive coupling and the driven coupling to be fitted together, and there is a concern that connection of the two portions cannot be performed smoothly.

The present invention has been devised while taking into consideration the aforementioned problems, and has the object of providing a medical manipulator, in which a portion on which the distal end working unit is disposed and a portion on which the drive source is disposed are capable of attachment and detachment to and from each other, and connection of the two portions can be performed smoothly.

For achieving the aforementioned object, the medical manipulator includes a handle, a shaft that is extended from the handle, a distal end working unit capable of operating with respect to the shaft, and a drive source for operating the distal end working unit. A first portion, which includes the distal end working unit and the shaft and on which a driven coupling is disposed, and a second portion, which includes the drive source and on which a drive coupling that is driven by the drive source is disposed, are capable of being attached and detached. In a state in which the first portion and the second portion are connected, the drive coupling and the driven coupling are fitted together, and a driving force of the drive source is transmitted to the distal end working unit. Further, on at least one of the drive coupling and the driven coupling, a tooth-end portion, on a side that initiates fitting between the drive coupling and the driven coupling when the first portion and the second portion are connected, becomes narrower toward an end surface thereof in an axial direction.

According to the above configuration, at a time of contact between the driven coupling and the drive coupling, even if the phases of the teeth thereof overlap, accompanying relative rotation between the driven coupling and the drive coupling, both of the couplings are fitted together along the tooth surfaces of the tooth-end portions, which become narrower toward the end surfaces in the axial direction. Consequently, fitting between the drive coupling and the driven coupling is carried out reliably and easily, and the connection of the first portion and the second portion can be performed smoothly.

In this case, the first portion may comprise a manipulator main body including a handle, and the second portion may comprise a drive unit that is capable of attachment and detachment with respect to the handle. In accordance with this configuration, in a medical manipulator, in which a common drive unit can be mounted and used with respect to handles having different functions and shapes, the drive unit can easily and reliably be attached to the handle.

The tooth-end portion may be disposed on the drive coupling. According to this configuration, as to the drive coupling and the driven coupling, the tooth-end portions, which become narrower toward end surfaces thereof in the axial direction, are provided on the drive coupling. Thus, with respect to any handles having different functions and shapes, fitting between the drive coupling and the driven coupling can easily and reliably be carried out upon attachment of the drive unit.

As to the drive coupling and the driven coupling, in the coupling on which the tooth-end portion is disposed, a curve of a tooth shape thereof may form an involute curve. By this configuration, since the tooth-end portions become thinner continuously in the axial direction from the tooth shape, which is formed by an involute curve, fitting between the drive coupling and the driven coupling can be carried out more smoothly.

DETAILED DESCRIPTION OF THE INVENTION

Hereinafter, a preferred embodiment of a medical manipulator according to the present invention will be described in detail below with reference to the accompanying drawings.

Figure 1:
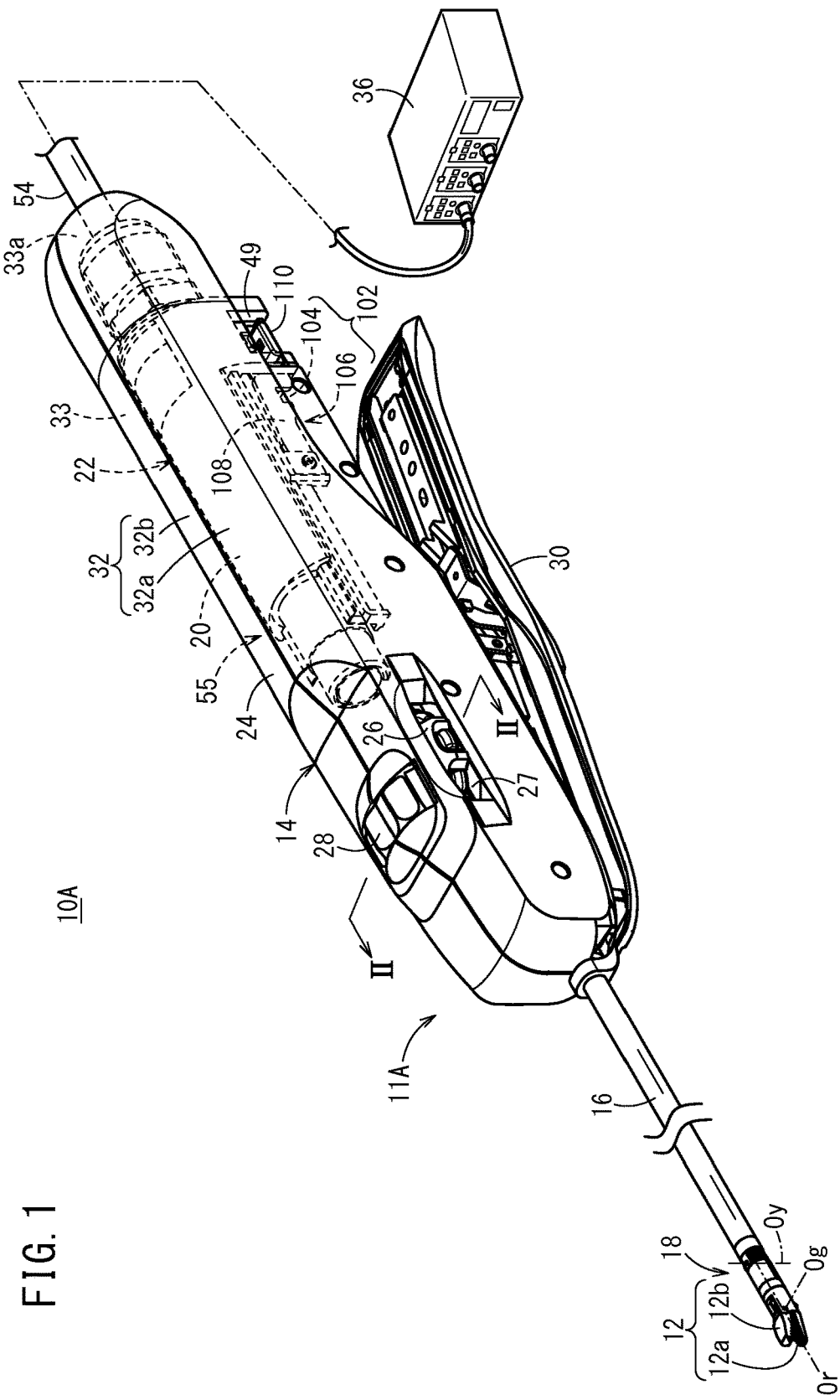
FIG. 1 is a perspective view with partial omission of a medical manipulator according to an embodiment of the present invention.

FIG. 1 is a perspective view with partial omission of a medical manipulator 10A (hereinafter referred to in abbreviated form as a "manipulator 10A") according to an embodiment of the present invention. The manipulator 10A is a medical device that grasps a needle, a thread, or a part of the living body or touches the living body using a gripper 12 (end effector) provided at the distal end thereof, and carries out a predetermined treatment.

The manipulator 10A comprises a handle 14 on which a plurality of input operating members are provided, a shaft 16 that extends from the handle 14, a distal end working unit 18 disposed on a distal end of the shaft 16 including a gripper 12, and a drive unit 22 in which a motor 20 (drive source) is provided for driving the distal end working unit 18, and which is capable of attachment and detachment to and from the handle 14. A manipulator main body 11A is made up from the handle 14, the shaft 16, and the distal end working unit 18.

In the foregoing manner, with the manipulator 10A according to the present embodiment, the manipulator main body 11A (first portion) and the drive unit 22 (second portion) can be attached and detached to and from each other. In a state in which the drive unit 22 is mounted on the handle 14 (hereinafter referred to as an "attached state"), when the motor 20 is driven, the driving force of the motor 20 is transmitted to the distal end working unit 18.

The manipulator 10A shown in FIG. 1 is constituted as a needle driver that is capable of grasping a medical needle (a curved needle or the like) with the gripper 12 disposed on the distal end thereof. The gripper 12 is a portion that carries out a surgical treatment, and in the illustrated example, the gripper 12 includes first and second gripper members 12a, 12b, and is configured to carry out opening and closing operations on the basis of a predetermined opening and closing operation axis Og. In the illustrated example, although concerning the gripper 12, a case has been described in which the first gripper member 12a is constituted as a fixed member and the second gripper member 12b is constituted as a movable member, both of the gripper members 12a, 12b may be constituted as movable members.

The posture of the distal end working unit 18 including the gripper 12 can be changed at a plurality of degrees of freedom with respect to the shaft 16. In the present embodiment, the distal end working unit 18 can carry out a "tilting operation" (swinging operation) in which the distal end working unit 18 is operated to tilt in left and right (transverse or lateral) directions with respect to an axis of the shaft 16 about a tilt axis Oy, and a "rolling operation" in which the distal end working unit 18 is rotated about the axial line (roll axis Or) in the longitudinal direction of the distal end working unit 18. The tilt axis Oy is not limited to being set in the vertical direction, and the tilt axis Oy may be set in a different direction that intersects the axis of the shaft 16.

The shaft 16 is an oblong small diameter tubular member that connects the handle 14 and the distal end working unit 18. In FIG. 1, a portion of the shaft 16 is omitted from illustration, and the shaft is rendered shorter than it actually is. A plurality of members configured to make up a power transmission mechanism are inserted through and arranged in a hollow portion of the shaft 16. Such a power transmission mechanism transmits, from the handle 14 to the distal end working unit 18, power that is necessary for carrying out the opening and closing operation of the gripper 12, and the rolling operation and the tilting operation of the distal end working unit 18. A structure may be provided in which one or a plurality of joints are provided at an intermediate location in the longitudinal direction of the shaft 16 to enable the tilting operation by the joints. Further, a structure may be provided in which the rolling operation is enabled at the proximal end of the shaft 16, or at an intermediate location in the longitudinal direction of the shaft 16.

The handle 14 is a portion that is gripped by an operator during use of the medical manipulator 10A, and by input operating members (in the present embodiment, a later described tilt wheel 26, a rolling switch 28, and a lever 30) being touched and operated by a finger, drives the distal end working unit 18 that is connected to the distal end of the shaft 16.

The handle 14 comprises a body portion 24 that is connected to a proximal end of the shaft 16, the tilt wheel 26 constituting a tilt operating unit that is provided on the body portion 24, the rolling switch 28 (input operating member) constituting a rolling operating unit that is provided on the body portion 24, and the lever 30 constituting an opening and closing operating unit that is provided on the body portion 24.

The body portion 24 makes up a part that is gripped by a user when the manipulator 10 is used. In the present embodiment, the body portion 24 is constituted in the form of a stick that extends over a certain length in the axial direction of the shaft 16. The body portion 24 includes a casing 32 made up from a left cover 32a and a right cover 32b, with frames, drive components (pulleys, gears, wires, etc.) or the like being arranged in the interior of the casing 32. For insertion and installation of the drive unit 22 in the interior of the casing 32 from the rear side, a rearwardly open installation hole 33 (see also FIG. 4) is formed.

The tilt wheel 26 for carrying out a tilting operation of the distal end working unit 18 is disposed near the center in the longitudinal direction of the body portion 24, and is rotatable about the vertically oriented axis of the handle 14. The tilt wheel 26 is constituted as a manual operating member, such that the tilt wheel 26 partially protrudes from openings 27 provided on left and right sides of the casing 32.

When the tilt wheel 26 is operated by being rotated, the operating force applied thereto is transmitted mechanically to the distal end working unit 18 through a tilting operation power transmission system, which is disposed internally in the handle 14 and the shaft 16, whereupon the distal end working unit 18 is tilted about an axis (tilt axis Oy) in a non-parallel direction with respect to the axis of the shaft 16. More specifically, when the tilt wheel 26 is rotated clockwise as viewed in plan, the distal end working unit 18 is tilted in a rightward direction about the handle 14, whereas when the tilt wheel 26 is rotated counterclockwise as viewed in plan, the distal end working unit 18 is tilted in a leftward direction about the handle 14.

With the manipulator 10A of the illustrated example, the rolling switch 28 for carrying out a rolling operation of the distal end working unit 18 is disposed on an upper portion in the vicinity of the distal end of the body portion 24. In the present embodiment, the rolling switch 28 is constituted as an electrical manipulating portion, which supplies an operating command to the motor 20 through a controller 36. Because the rolling switch 28 is an electrical switch, the rolling switch 28 is not limited to the location shown in FIG. 1, but can be arranged in a different location of the handle 14.

In a state in which the drive unit 22 is mounted in the handle 14, and the power source of the controller 36 is turned on, when the rolling switch 28 is operated and moved, the operating state (position) of the rolling switch 28 is detected by the controller 36, the motor 20 is driven under the controlling action of the controller 36, and by the driving force of the motor 20 being transmitted to the distal end working unit 18, the distal end working unit 18 is rotated about the longitudinal axis (roll axis Or) of the distal end working unit 18.

Figure 2:
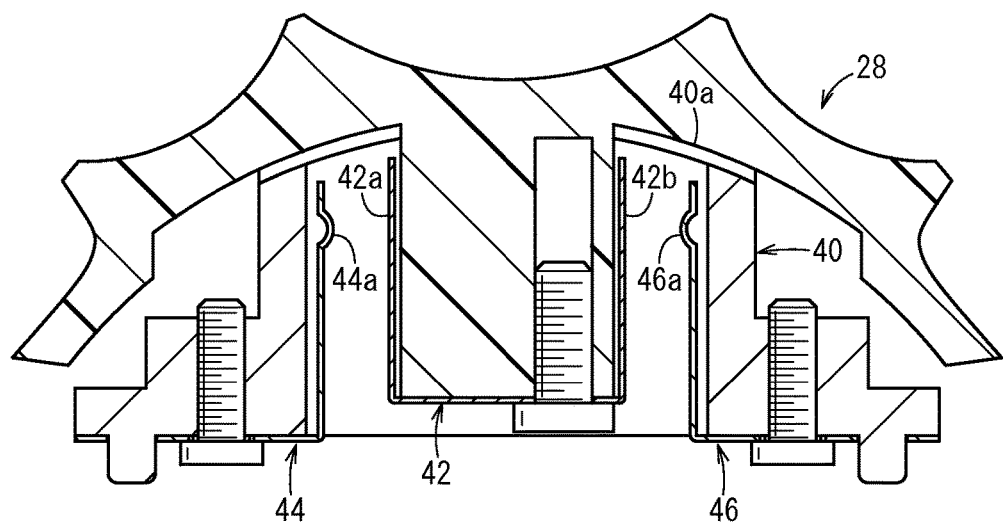
FIG. 2 is a transverse cross-sectional view of a switch structure taken along line II-II of FIG. 1.

FIG. 2 is a cross-sectional view showing a switch structure including the rolling switch 28, which is a transverse cross-sectional view taken along line II-II of FIG. 1. In FIG. 2, portions apart from the switch structure of the handle 14 are omitted from illustration. In the present illustrated example, on a switch pedestal 40 having an arcuate slide surface 40a, the rolling switch 28 is arranged swingably in a lateral direction. In another structural example, the rolling switch 28 may be supported through a rotating shaft on a switch support member, and thereby arranged in a swingable manner.

A movable-side contact member 42 is disposed on the rolling switch 28, and on the side of the switch pedestal 40, first and second fixed-side contact members 44, 46 are disposed facing the movable-side contact member 42. The rolling switch 28 is biased by a non-illustrated spring elastically toward a neutral position in the transverse direction, and in a state in which the rolling switch 28 is not pressed in the transverse direction, the rolling switch 28 maintains the neutral position (the position shown in FIG. 2) under an elastic action thereof.

When the rolling switch 28 is positioned in the neutral position, the movable-side contact member 42 remains out of contact with respect to either one of the first and second fixed-side contact members 44, 46, and the rolling operation of the distal end working unit 18 is not performed.

When the rolling switch 28 is operated to move the switch pedestal 40 in a leftward direction, a first contact point 42a of the movable-side contact member 42 comes into contact with a contact point 44a of the first fixed-side contact member 44, whereupon the operating state of the rolling switch 28 is detected by the controller 36, and under a drive control of the motor 20 by the controller 36, the distal end working unit 18 is rotated to the left.

When the rolling switch 28 is operated to move the switch pedestal 40 in a rightward direction, a second contact point 42b of the movable-side contact member 42 comes into contact with a contact point 46a of the second fixed-side contact member 46, whereupon the operating state of the rolling switch 28 is detected by the controller 36, and under a drive control of the motor 20 by the controller 36, the distal end working unit 18 is rotated to the right.

A lever 30 for performing an opening and closing operation of the gripper 12 is disposed on a lower part of the body portion 24, and is swingably mounted upward and downward about the distal end side thereof which serves as a support point. According to the present embodiment, the lever 30 is constructed as a manual operating member, in which an opening and closing operation of the gripper 12 is carried out by mechanically transmitting to the gripper 12 of the distal end working unit 18 an operating force applied with respect to the lever 30. More specifically, a structure is provided in which the gripper 12 is opened when the lever 30 is opened, and the gripper 12 is closed when the lever 30 is closed.

As shown in FIG. 1, the drive unit 22 of the manipulator 10A is used in a condition of being connected to the controller 36 through a cable 54. The controller 36 controls the supply of power and driving or the like of the motor 20, and receives electrical power from an external power source. In a state in which the drive unit 22 is mounted on the handle 14, when the rolling switch 28 is operated, the controller 36 controls driving of the motor 20 in response to operation thereof. The rotation of the motor 20 may be detected, and the motor 20 may be feedback controlled through the controller 36.

The form of use can be one in which, concerning the manipulator 10A that is constructed in the foregoing manner, the manipulator main body 11A can be discarded after being used a predetermined number of times, whereas the drive unit 22 can be used repeatedly many times by changing the manipulator main body 11A that is connected to the drive unit 22.

Figure 3:
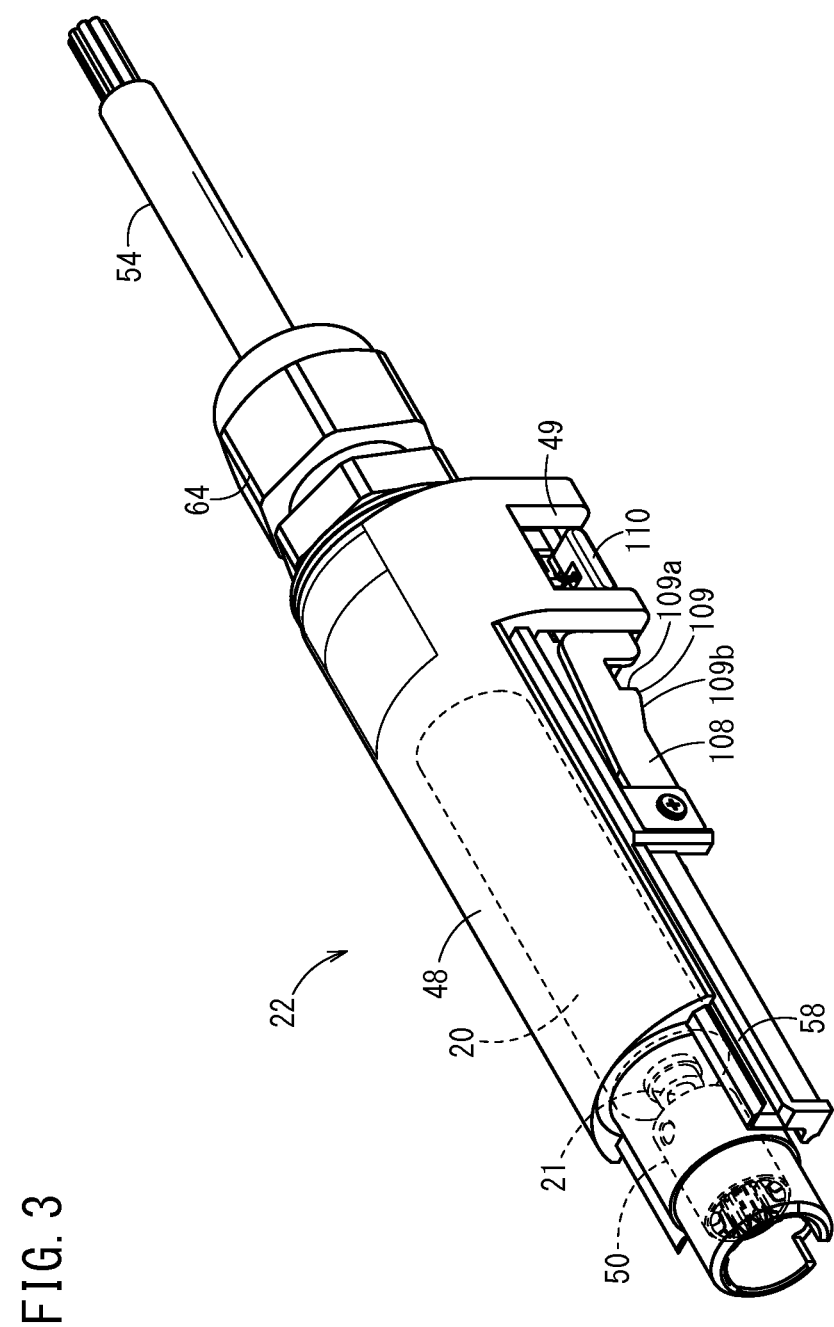
FIG. 3 is a perspective view of a drive unit of the medical manipulator illustrated in FIG. 1.
Figure 4:
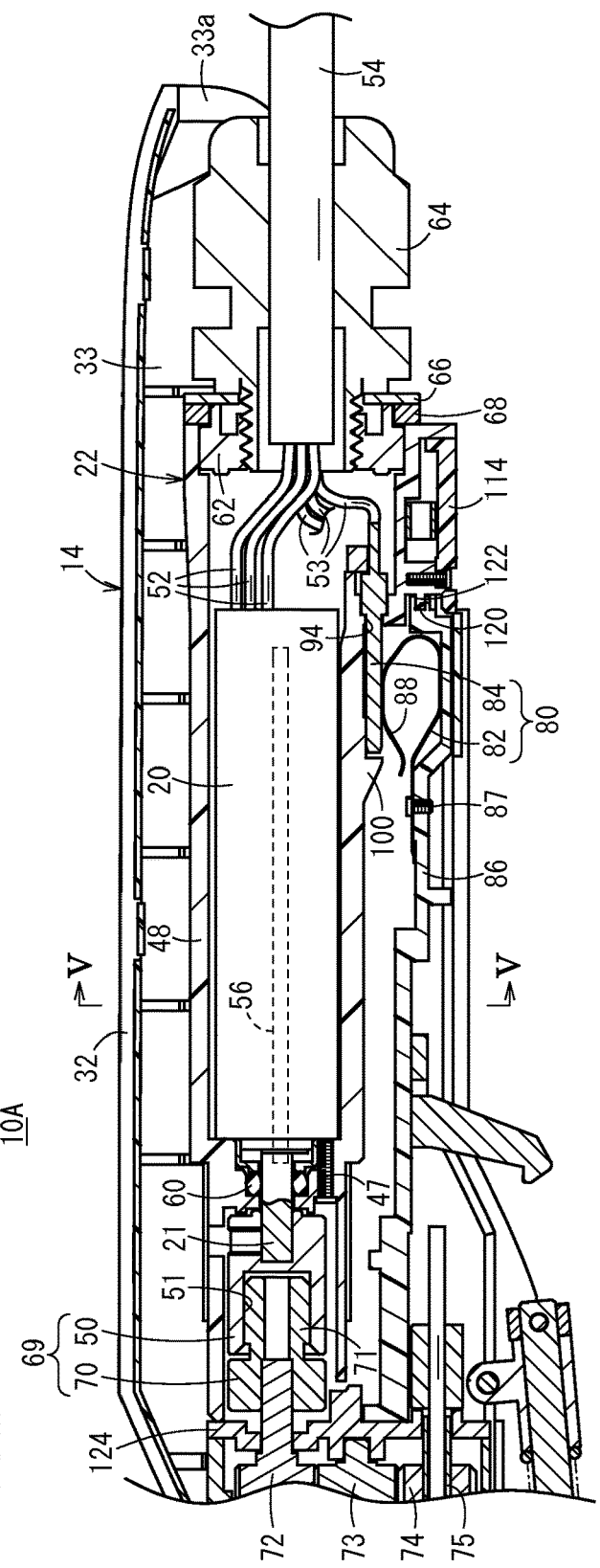
FIG. 4 is a vertical cross-sectional view with partial omission of a proximal end side of the medical manipulator illustrated in FIG. 1.

FIG. 3 is a perspective view of the drive unit 22. FIG. 4 is a vertical cross-sectional view with partial omission of a proximal end side of the medical manipulator 10A. The drive unit 22 includes a housing 48, the motor 20 (drive source) disposed inside the housing 48, and a drive coupling 50 (drive member) that is fixed to an output shaft 21 of the motor 20. The cable 54 including a plurality of power lines 52 and signal lines 53 is connected to the proximal end side of the drive unit 22. Inside the housing 48, the power lines 52 are connected to the motor 20, and the signal lines 53 are connected to a plurality of unit-side terminal members 84, to be discussed later.

Figure 5:
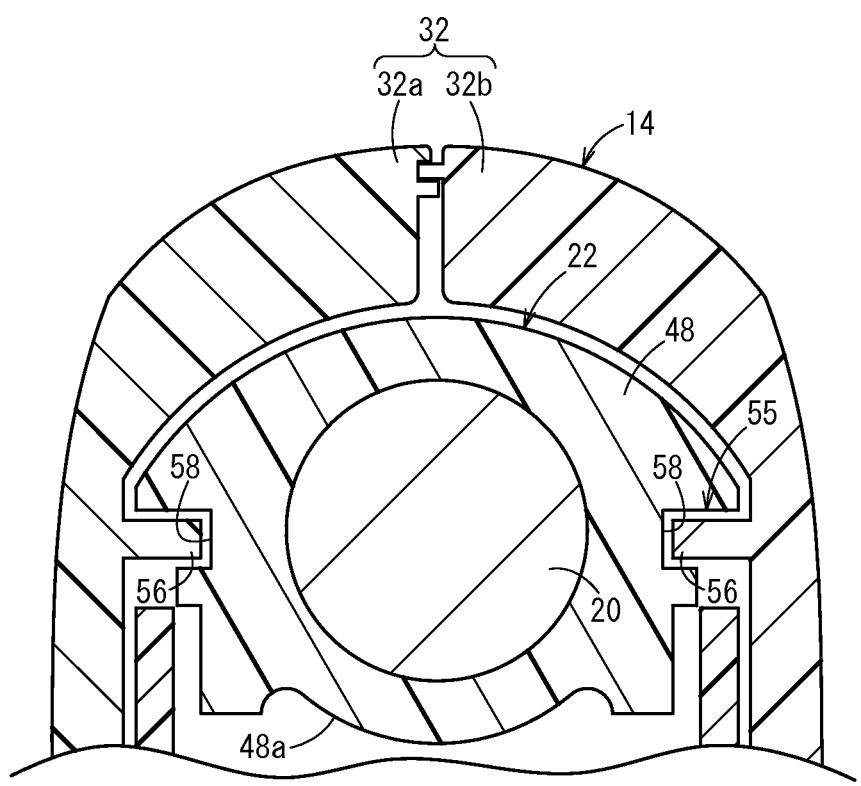
FIG. 5 is a transverse cross-sectional view taken along line V-V of FIG. 4.

As shown in FIG. 1, a guide mechanism 55, which guides movement of the drive unit 22 relative to the handle 14 when the drive unit 22 is attached and detached with respect to the handle 14, is connected to the manipulator 10A. FIG. 5 is a transverse cross-sectional view taken along line V-V of FIG. 4. As shown in FIGS. 4 and 5, the guide mechanism 55 includes guide rails 56 disposed on the handle 14, and guide receiving members 58 disposed on the drive unit 22 and which are capable of sliding along the guide rails 56.

More specifically, as shown in FIG. 5, the guide rails 56 project out respectively from left and right inner surfaces of the casing 32, and extend along a longitudinal direction of the handle 14. The guide receiving members 58 are disposed as groove-like shapes on left and right outer side surfaces of the housing 48 of the drive unit 22, and extend longitudinally along the drive unit 22. As shown in FIG. 3, distal ends of the guide receiving members 58 are open at a distal end of the housing 48.

In the present embodiment, the motor 20 is housed hermetically in the interior of the housing 48. More specifically, as shown in FIG. 4, a ring-shaped first seal member 60 is arranged on a distal end inner circumferential portion of the housing 48, and an inner circumferential portion of the first seal member 60 is placed in slidable contact hermetically with an outer circumferential portion of the output shaft 21 of the motor 20. At a proximal end part of the housing 48, a ring-shaped lid member 62 is screw-engaged and fixed, and a hollow cable connecting member 64 is screw-engaged and fixed in the lid member 62. A washer 66 is gripped between the cable connecting member 64 and the lid member 62, and a ring-shaped second seal member 68 is interposed between the washer 66 and the housing 48. The cable connecting member 64 is constituted from a plurality of components. A liquidtight and airtight seal is formed between the cable 54 and the cable connecting member 64.

In this manner, by the first seal member 60 that is provided on the distal end side of the housing 48, a hermetic seal is maintained between the motor 20 and the housing 48, and by the second seal member 68 that is provided on the proximal end side of the housing 48, the proximal end side of the housing 48 is hermetically sealed and closed. Further, the housing 48 and the motor 20 are fixed together mutually by a screw 47 (see FIG. 4). Between the screw 47 and a hole 48b of the housing 48 through which the screw 47 is inserted, an adhesive is filled in an airtight manner. Furthermore, between a plurality of later-described unit-side terminal members 84 and insertion holes 94 into which the unit-side terminal members 84 are inserted, an adhesive is filled in an airtight manner. By the above constitution, a hermetically sealed condition, i.e., airtightness, is secured in the interior of the housing 48.

As shown in FIG. 4, in a state in which the drive unit 22 is attached to the handle 14, the drive coupling 50 (drive member), which is fixed to the output shaft 21 of the motor 20, is fitted (enmeshed) with a driven coupling 70 disposed on the side of the handle 14. By the drive coupling 50 and the driven coupling 70, a power coupling 69 is constituted whereby, in a state in which the drive unit 22 is attached to the handle 14, a rotary driving force of the motor 20 is transmitted to the side of the handle 14.

In the present embodiment, a plurality of gear teeth 51 are provided, which are arrayed circumferentially on an inner circumferential portion of the drive coupling 50, and a plurality of gear teeth 71 are provided, which are arrayed circumferentially on an outer circumferential portion of the driven coupling 70. The drive coupling 50 and the driven coupling 70 are engaged together coaxially. The driven coupling 70 is fixed to a gear shaft 72 provided in the handle 14. A rotational force, which is input from the drive coupling 50 to the driven coupling 70, is transmitted to the gear shaft 72, and further is transmitted to the distal end working unit 18 via another gear shaft 73 disposed in the handle 14, a gear tube 74 that is enmeshed with the gear shaft 73, and a torque-transmitting pipe 75 that is fixed coaxially with the gear tube 74.

Figure 6:
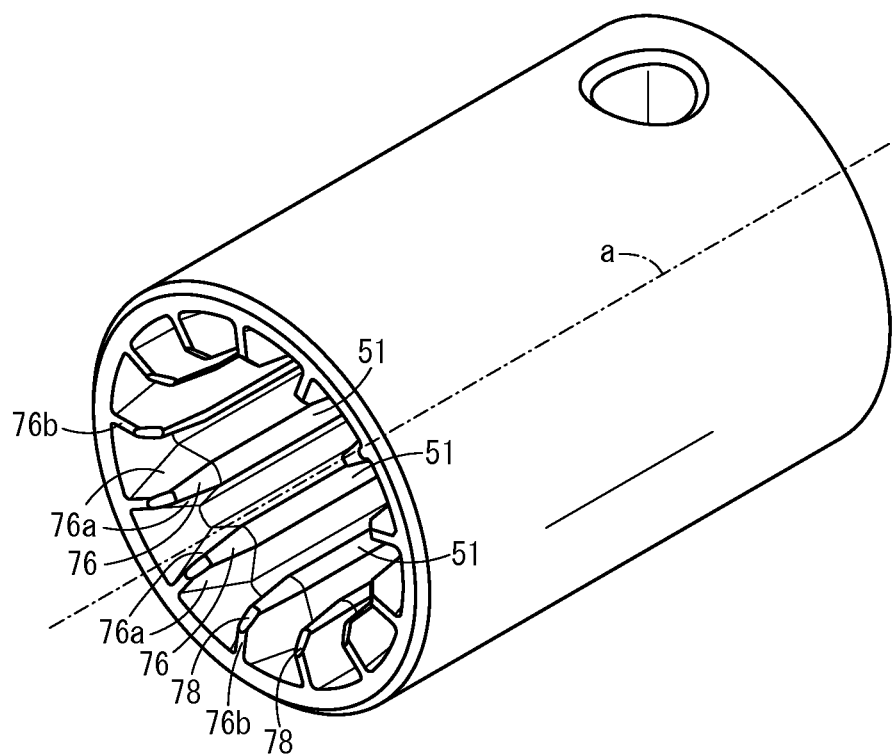
FIG. 6 is a perspective view of a drive coupling in the drive unit.

FIG. 6 is a perspective view of the drive coupling 50. Below, in relation to the drive coupling 50 and the constituent components thereof, an open side of the drive coupling 50 will be referred to as a distal end side or a distal end direction. In the present illustrated example, in the drive coupling 50, the curve of the tooth shape forms an involute curve.

On the respective teeth 51 of the drive coupling 50, tooth-end portions 76 (in the case of the illustrated example, distal end tooth portions in the direction of the axial line "a"), on a side that initiates fitting when the drive coupling 50 and the driven coupling 70 are connected, are shaped to taper into rectangular ribs toward the distal end side from the involute tooth shape. Stated otherwise, tooth surfaces 76a on both sides of the respective tooth-end portions 76 are not parallel to the axial line "a" of the drive coupling 50, but rather are tilted with respect to the axial line "a" so as to approach mutually in a circumferential direction in the direction of the distal end. Consequently, the widths of the respective tooth-end portions 76 become smaller (narrower) toward the distal end side (on the side of end surfaces 76b thereof in the direction of the axial line "a") of the drive coupling 50.

Furthermore, on the tooth-end portions 76 of the respective teeth 51, tapered portions 78 are provided, which are tilted so as to be displaced radially-outwardly toward the direction of the distal end of the drive coupling 50.

In the present illustrated example, the drive coupling 50 is constituted as a female coupling, and the driven coupling 70 is constituted as a male coupling. However, in a modification of the present embodiment, the drive coupling 50 may be constituted as a male coupling, and the driven coupling 70 may be constituted as a female coupling. Further, in the illustrated example, the tooth-end portions 76, which narrow toward the end surfaces 76b in the axial direction, are disposed on the drive coupling 50. However, in another modification of the present embodiment, similar tooth-end portions, which narrow toward the end surfaces (proximal end surfaces) in the axial direction, may be disposed on the driven coupling 70.

As shown in FIG. 4, in the manipulator 10A, there is further provided an electrical connection mechanism 80 that electrically connects the handle 14 and the drive unit 22 accompanying attachment of the drive unit 22 to the handle 14. The electrical connection mechanism 80 includes handle-side terminal members 82 made up from a conductive material disposed on the handle 14, and unit-side terminal members 84 made up from a conductive material disposed on the drive unit 22. The handle-side terminal members 82 and the unit-side terminal members 84 preferably are constituted from a material that resists corrosion, for example, stainless steel, titanium, a titanium alloy, etc.

Figure 7A:
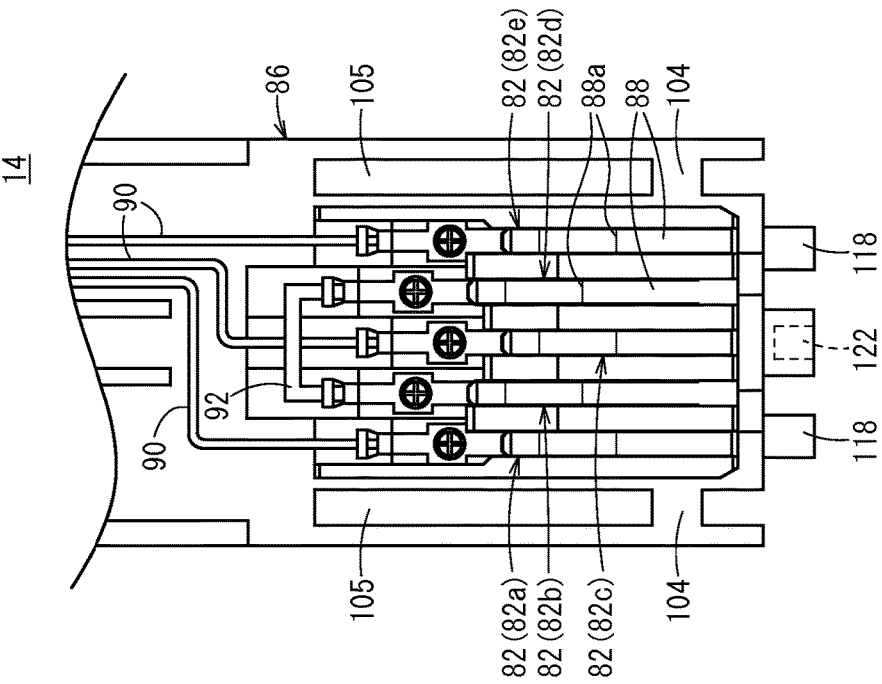
FIG. 7A is a perspective view, as seen from an oblique rearward direction, of a state of arrangement of a handle-side terminal member.
Figure 7B:
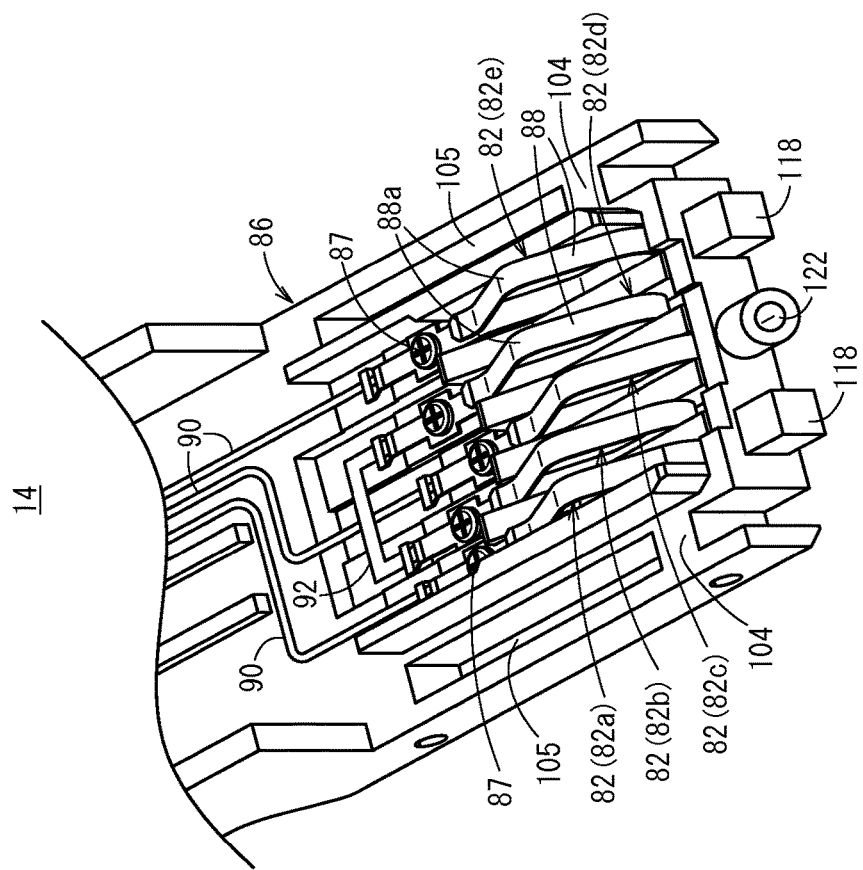
FIG. 7B is a plan view showing a state of arrangement of the handle-side terminal member.

In the handle 14, a unit holder 86 is provided that extends in forward and rearward directions of the handle 14. On an upper surface of a proximal end side of the unit holder 86, a plurality of the handle-side terminal members 82 is provided. As shown in FIGS. 7A and 7B, in the present illustrated example, five handle-side terminal members 82a to 82e are arranged at intervals in the widthwise direction (lateral direction) of the handle 14.

Each of the handle-side terminal members 82 is fixed to the unit holder 86 by a fixing part 87 (screw) at a distal end side thereof, and elastically deformable elastic pieces 88, which are folded back upwardly and around toward the distal end, are provided on proximal end sides of the handle-side terminal members 82. The elastic pieces 88 include portions that are convexly shaped upwardly, and the convexly shaped apex portions 88a thereof come into contact with the unit-side terminal members 84. The elastic pieces 88, instead of being disposed on the handle-side terminal members 82, may be disposed on the unit-side terminal members 84. The handle-side terminal members 82 of the present illustrated example are constituted integrally by spring elements for pressing the terminals, and electrically conductive elements. However, a structure can be adopted in which the spring elements and the electrically conductive elements are two separate members. In this case, for example, the handle-side terminal members 82 may be constituted from conductive terminal main bodies, which are arranged displaceably, and springs for pressing the main bodies. The springs need not be metallic, but may be made from carbon or resin. Further, the shape of the springs is not particularly limited. Plate springs, helical springs, or the like may be used.

As shown in FIG. 7A, among the five handle-side terminal members 82a to 82e, the centrally disposed handle-side terminal member 82c is arranged at a lowest position, the handle-side terminal members 82b, 82d disposed adjacent to both sides of the handle-side terminal member 82c are arranged at positions higher than the central handle-side terminal member 82c, and the outermost disposed handle-side terminal members 82a, 82e are arranged at positions higher than the handle-side terminal members 82b, 82d that lie inwardly adjacent thereto.

As will be discussed later, the two handle-side terminal members 82b, 82d function as detection terminals for detecting attachment and detachment of the drive unit 22. As shown in FIG. 7B, among the five handle-side terminal members 82a to 82e, the two handle-side terminal members 82b, 82d that function as detection terminals are arranged at positions shifted more frontward (toward the distal end side) than the remaining handle-side terminal members 82a, 82c, 82e.

The central handle-side terminal member 82c and the two handle-side terminal members 82a, 82d on outer sides thereof are capable of conducting electricity, through respective lead wires 90 connected thereto, to the movable-side contact member 42 of the rolling switch 28, and first and second fixed-side contact members 44, 46 shown in FIG. 2. More specifically, when the movable-side contact member 42 and the first fixed-side contact member 44 are in contact, electricity is conducted between the central handle-side terminal member 82c and the left handle-side terminal member 82a. Further, when the movable-side contact member 42 and the second fixed-side contact member 46 are in contact, electricity is conducted between the central handle-side terminal member 82c and the right handle-side terminal member 82e.

In a state in which the drive unit 22 is mounted on the handle 14, when the rolling switch 28 is positioned in a neutral position, because the central handle-side terminal member 82c is not electrically connected to either one of the left and right handle-side terminal members 82a, 82e, the controller 36 performs a control to place the motor 20 in a stopped condition.

When the rolling switch 28 is operated to move in a leftward direction, electricity is conducted between the central handle-side terminal member 82c and the left handle-side terminal member 82a. Such a condition is detected by the controller 36, whereupon the controller 36 controls driving of the motor 20, and in the distal end working unit 18, a left-handed rolling operation is carried out.

When the rolling switch 28 is operated to move in a rightward direction, electricity is conducted between the central handle-side terminal member 82c and the right handle-side terminal member 82e. Such a condition is detected by the controller 36, whereupon the controller 36 controls driving of the motor 20, and in the distal end working unit 18, a right-handed rolling operation is carried out.

In this manner, the handle-side terminal members 82 function as switch terminals (operation terminals) for detecting the operating state of the rolling switch 28.

The other two handle-side terminal members 82b, 82d are electrically connected via a short-circuiting member 92. The handle-side terminal members 82b, 82d function as detection terminals for detecting whether or not the drive unit 22 has been attached with respect to the handle 14.

In the present illustrated example, among the five handle-side terminal members 82a to 82e, the switch terminal and the detection terminal are arranged alternately one by one. However, the manner of arrangement thereof is not limited, and the switch terminal and the detection terminal may be arranged in any manner.

Figure 8:
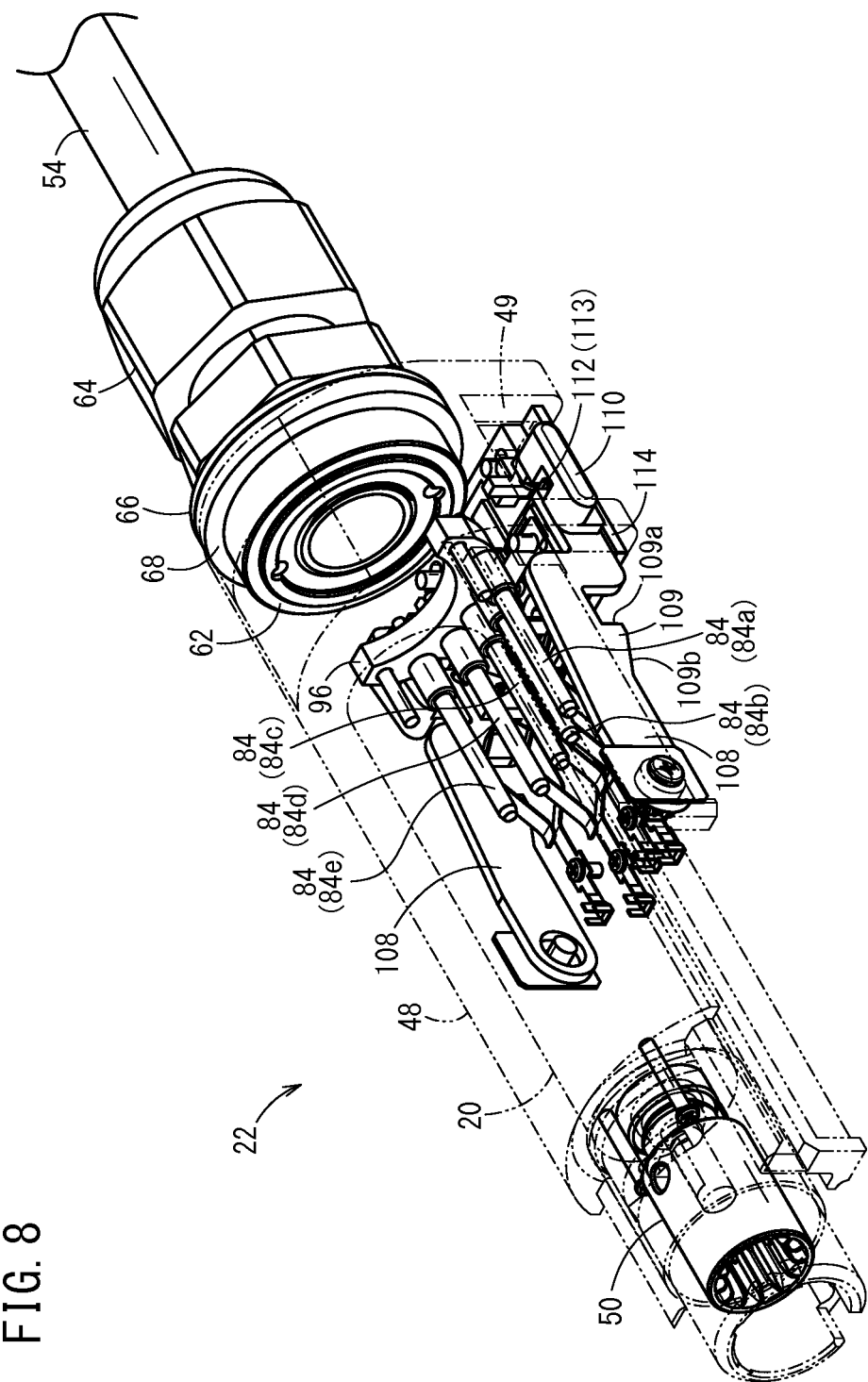
FIG. 8 is a perspective view of the drive unit, shown partially with phantom lines.
Figure 9:
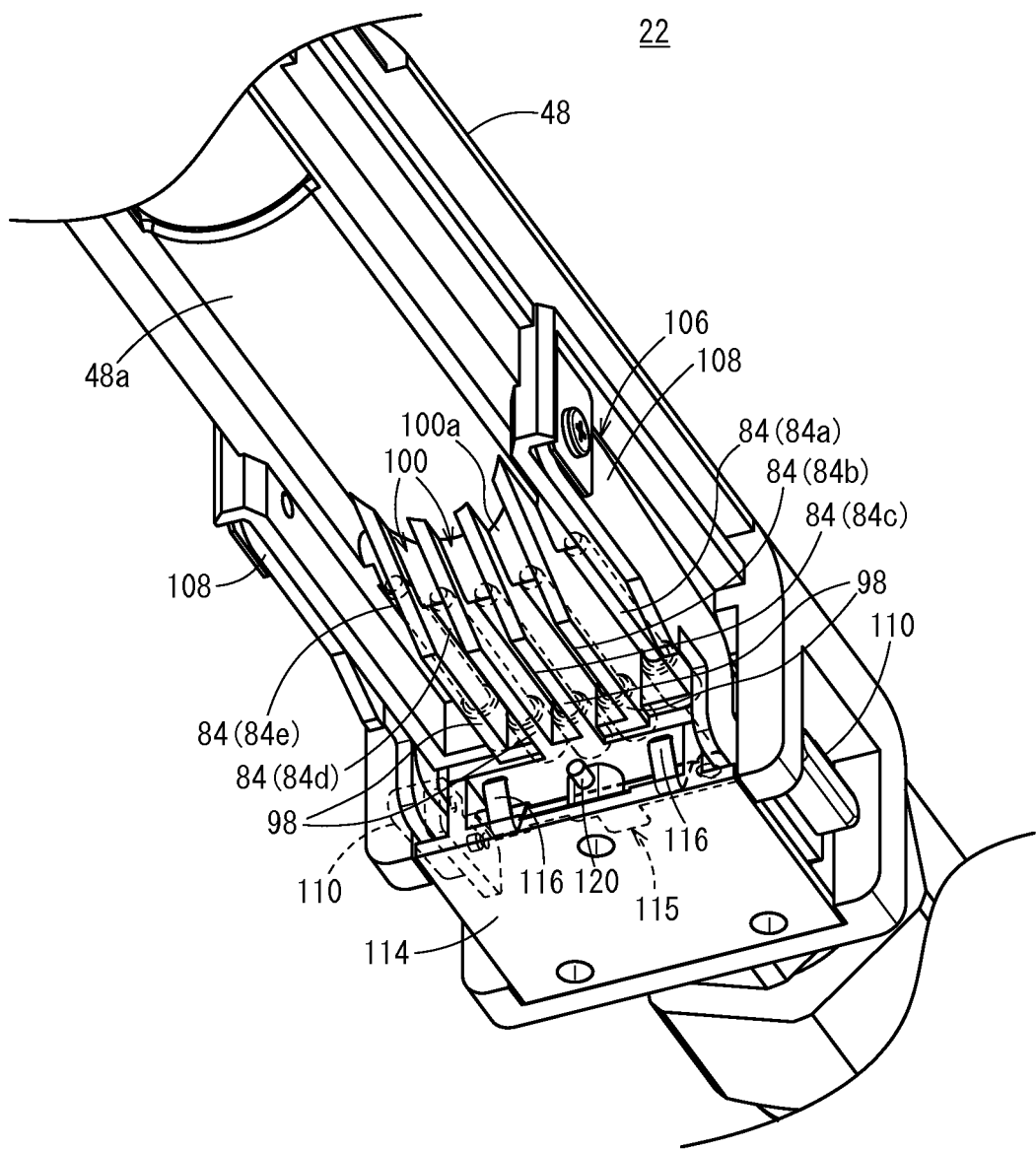
FIG. 9 is a perspective view, as seen obliquely from below, of the drive unit.

Next, the unit-side terminal members 84 will be described. FIG. 8 is a perspective view of the drive unit 22, which is shown partially by phantom lines. FIG. 9 is a perspective view as seen obliquely from below the drive unit 22. In the present embodiment, five unit-side terminal members 84a to 84e are disposed mutually in parallel and with intervals therebetween in the circumferential direction of the motor 20. The respective unit-side terminal members 84 are shaped in the form of elongate narrow pins, with the longitudinal directions thereof being arranged along the longitudinal direction of the drive unit 22. The respective unit-side terminal members 84 may be plate-shaped.

Proximal end sides of the respective unit-side terminal members 84 are retained by spacers 96 that are fixed to the housing 48.

The respective unit-side terminal members 84 are fixed to the housing 48 in a state of penetrating through the insertion holes 94 (see FIG. 4) that are disposed in the housing 48. As shown in FIG. 4, distal end sides of the respective unit-side terminal members 84 project out from the insertion holes 94, and protrude from the housing 48 on the lower surface side of the housing 48.

In a state in which the drive unit 22 is mounted on the handle 14, the central unit-side terminal member 84c and the outermost unit-side terminal members 84a, 84e are in contact with the central handle-side terminal member 82c and the outermost handle-side terminal members 82a, 82e (switch terminals) provided on the handle 14, whereas the remaining two unit-side terminal members 84b, 84d are in contact with the two handle-side terminal members 82b, 82d (detection terminals) provided on the handle 14.

On a lower portion of the housing 48, at intervals in the widthwise direction of the housing 48, a plurality of (four) partition walls 98 are provided that extend in the longitudinal direction of the housing 48 and project downwardly therefrom. Distal end side portions of the unit-side terminal members 84 are arranged with respective gaps between the partition walls 98.

Further, on a lower portion of the housing 48, at a position in front of the respective unit-side terminal members 84, a plurality of downwardly projecting protrusions 100 are provided so as to face the distal ends of the unit-side terminal members 84. The protrusions 100 include tapered lower surfaces 100a that are tilted so as to be displaced downwardly toward the rear.

As shown in FIG. 1, in the manipulator 10A, there is further provided a lock mechanism 102 that restricts the drive unit 22 so as not to become detached from the handle 14, in a state in which the drive unit 22 has been attached to the handle 14. In the present embodiment, the lock mechanism 102 includes engagement members 104 disposed on the handle 14, and a lever device 106 disposed on the drive unit 22.

Accompanying attachment of the drive unit 22 to the handle 14, portions of the lever device 106 engage with the engagement members 104, whereby the drive unit 22 is prevented from becoming detached and separating away from the handle 14. On the other hand, by releasing the engagement between the engagement members 104 and the lever device 106, the drive unit 22 is capable being detached from the handle 14. More specifically, the lock mechanism 102 is constituted in the manner described below.

As shown in FIG. 7A, the engagement members 104 in the lock mechanism 102 are disposed on both left and right sides of a proximal end portion of the unit holder 86. In the present illustrated example, elongate grooves 105 are formed on both left and right sides of the proximal end portion of the unit holder 86, and portions on proximal end sides of the grooves 105 function as the engagement members 104.

Figure 10:
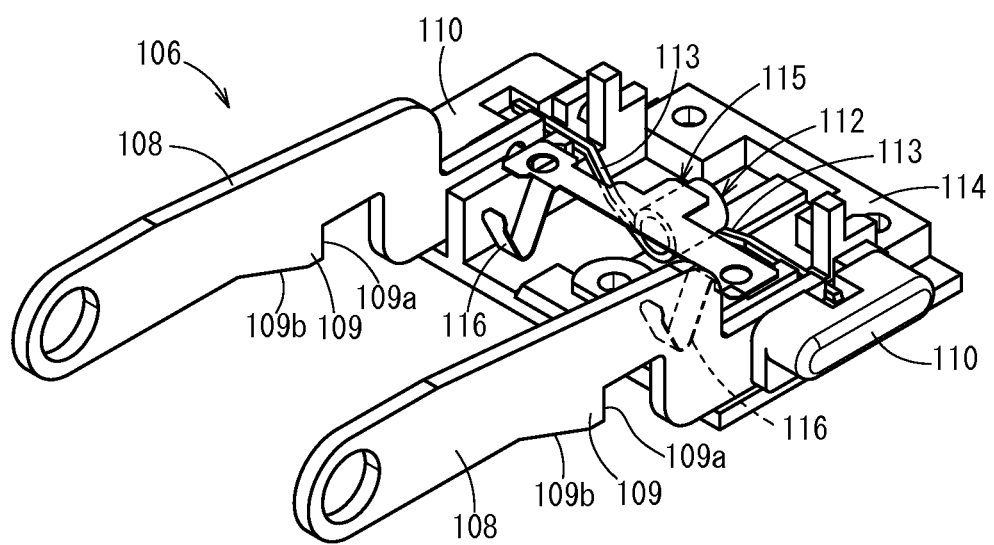
FIG. 10 is a perspective view of a lever device.

As shown in FIG. 10, the lever device 106 in the lock mechanism 102 includes lever members 108, distal end parts of which are connected swingably with respect to the housing 48, and being bent in crank-like shapes at intermediate regions in the longitudinal direction thereof, operating tabs 110 fixed to proximal end outer sides of the lever members 108, and a biasing member 112 that biases the lever members 108 elastically downward.

The lever members 108 and the operating tabs 110 are disposed in a pair to the left and right of the drive unit 22. The left and right lever members 108 are capable of swinging with respect to the housing 48 independently of one another. On each of the lever members 108, downwardly projecting engagement pawls 109 are disposed more on the distal end side than the portions thereof that are bent in crank-like shapes.

The drive unit 22 is inserted from a proximal end side of the handle 14, and when advanced up to a predetermined position, proximal end surfaces 109a of the engagement pawls 109 become hooked over the engagement members 104 (see FIG. 7A) provided on the handle 14. As a result, a locked state is brought about in which movement of the drive unit 22 in the proximal end direction relative to the handle 14 is prevented. Further, tapered lower surfaces 109b, which are displaced upwardly toward the distal end direction of the lever members 108, are provided on the engagement pawls 109.

The operating tabs 110 project out to the left and right from the proximal end of the lever members 108, and protrude through openings 49 provided on both left and right side lower portions of the housing 48. Consequently, a user can directly touch and operate the operating tabs 110 that protrude from the openings 49. The biasing member 112 in the present illustrated example includes a pair of springs 113, which bias the left and right lever members 108 in a downwardly pressed manner.

As shown in FIG. 9, a lower cover 114 is fixed to a proximal end lower portion of the housing 48. Proximal end portions of the lever members 108 are biased elastically by the biasing member 112, and in a state of being pressed against the lower cover 114, are arranged between the housing 48 and the lower cover 114. The biasing member 112 is fixed to the lower cover 114.

In a state in which the drive unit 22 is mounted on the handle 14, when the operating tabs 110 are pressed upwardly, the lever members 108 are rotated upwardly in opposition to the elastic force of the biasing member 112, whereupon the engagement between the engagement pawls 109 and the engagement members 104 is released. Consequently, by releasing locking by the lock mechanism 102, the drive unit 22 is capable of being displaced in the proximal end direction relative to the handle 14.

Instead of the vertically swingably disposed lever members 108, according to a modified example, lever members constructed in the form of plate springs, which are elastically deformable in lateral (left and right) directions, may be disposed on both left and right sides, or on either the left or right side of the drive unit 22. In this case, engagement pawls (portions corresponding to the engagement pawls 109), which are capable of engaging with engagement members (portions corresponding to the engagement members 104) disposed on the handle 14, are provided on outer surfaces of the lever members according to the modified example.

A return spring member 115 is fixed to the lower cover 114. The return spring member 115 in the present illustrated example includes two elastic members 116 that are separated in the lateral direction, and in a state in which the drive unit 22 is attached to the handle 14, the elastic members 116 are pressed by pressing members 118 (see FIG. 7A) disposed on the proximal end of the unit holder 86, and thus are subjected to elastic compressive deformation. Accordingly, the occurrence of play or chattering between the handle 14 and the drive unit 22 can be prevented. If locking by the lock mechanism 102 is released to enable displacement of the drive unit 22 relative to the handle 14, accompanying the shapes of the elastic members 116 being resiliently restored, the drive unit 22 is moved in the proximal end direction by a slight amount with respect to the handle 14. A chattering prevention mechanism to prevent chattering between the pressing members 118 and the elastic members 116 may be provided at a location other than that shown in the present illustrated example.

As shown in FIG. 9, a positioning pin 120 that projects in the proximal direction is disposed on a proximal end side lower portion (specifically, the lower cover 114) of the housing 48. In a state in which the drive unit 22 is mounted on the handle 14, the positioning pin 120 is inserted into a positioning hole 122 (see FIG. 7A) disposed on the proximal end of the unit holder 86.

The positioning pin 120 may be disposed not on the housing 48, but on another portion (for example, on the lower cover 114) of the drive unit 22. The positioning hole 122 may be disposed not on the unit holder 86, but on another portion of the handle 14, for example, on the casing 32. Further, differing from the present illustrated example, the positioning hole 122 may be disposed on the side of the drive unit 22, and the positioning pin 120 may be disposed on the side of the handle 14.

In the manipulator 10A according to the present embodiment, only the rolling operation of the distal end working unit 18 is effected by an electrical drive provided through the motor 20, whereas the tilting operation and the opening/closing operation of the distal end working unit 18 are effected by a manual drive. However, in a modification of the manipulator 10A, a structure may be provided in which not only the rolling operation, but also one or both of the tilting operation and the opening/closing operation are effected by an electrical drive.

Next, operations of the manipulator 10A, which is constructed in the foregoing manner, will be described.

Figure 11:
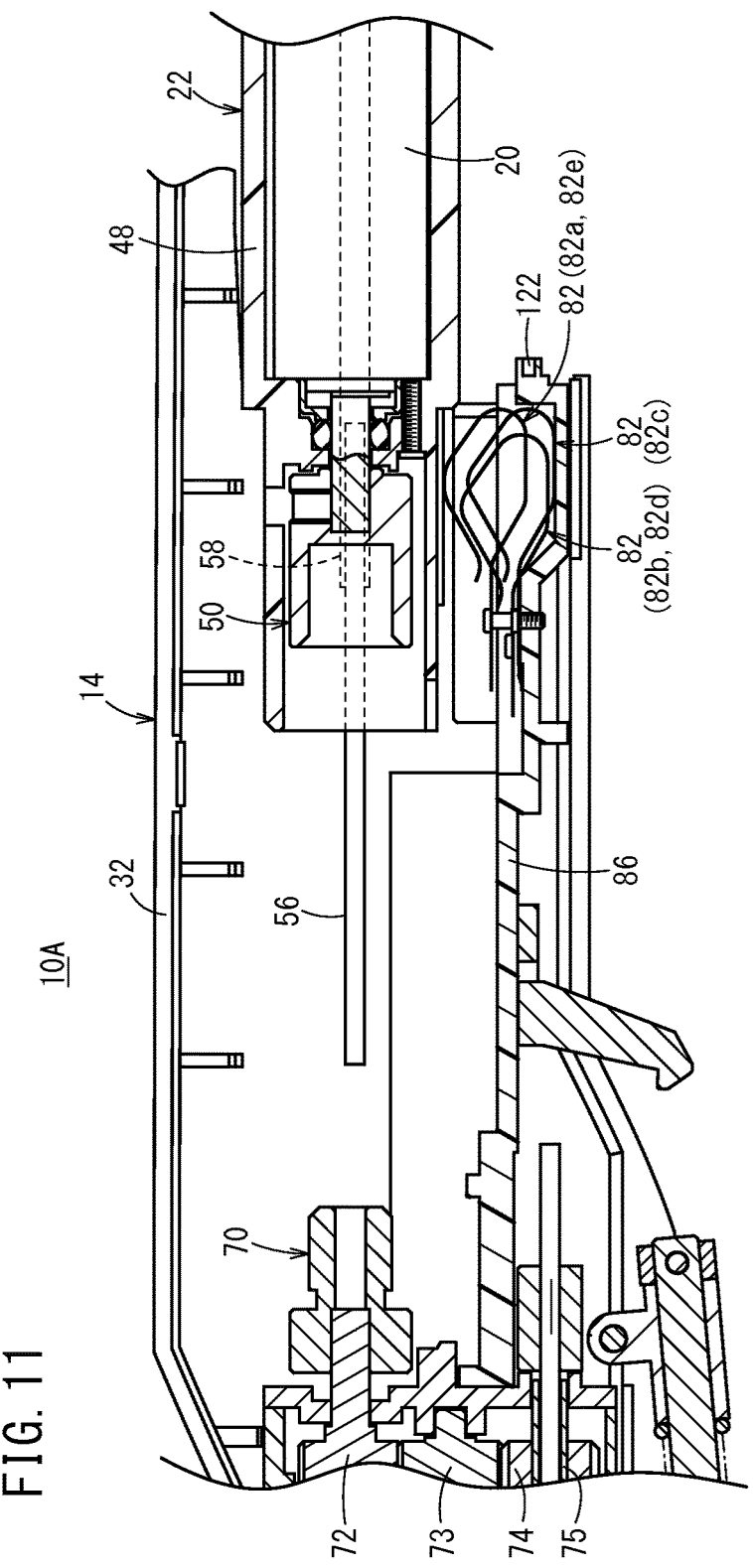
FIG. 11 is an explanatory drawing showing a positional relationship between the handle and the drive unit, when the drive unit starts to be attached to the handle.

During use of the manipulator 10A, the drive unit 22 is attached to the handle 14. As shown in FIG. 11, when the drive unit 22 starts to be inserted from the proximal end side of the handle 14, the guide rails 56 disposed on the handle 14 are inserted into the guide receiving members 58 (see also FIG. 3) disposed on the drive unit 22. Consequently, under a guiding action by the guide rails 56 and the guide receiving members 58, the drive unit 22 can be inserted smoothly into the handle 14.

Figure 12:
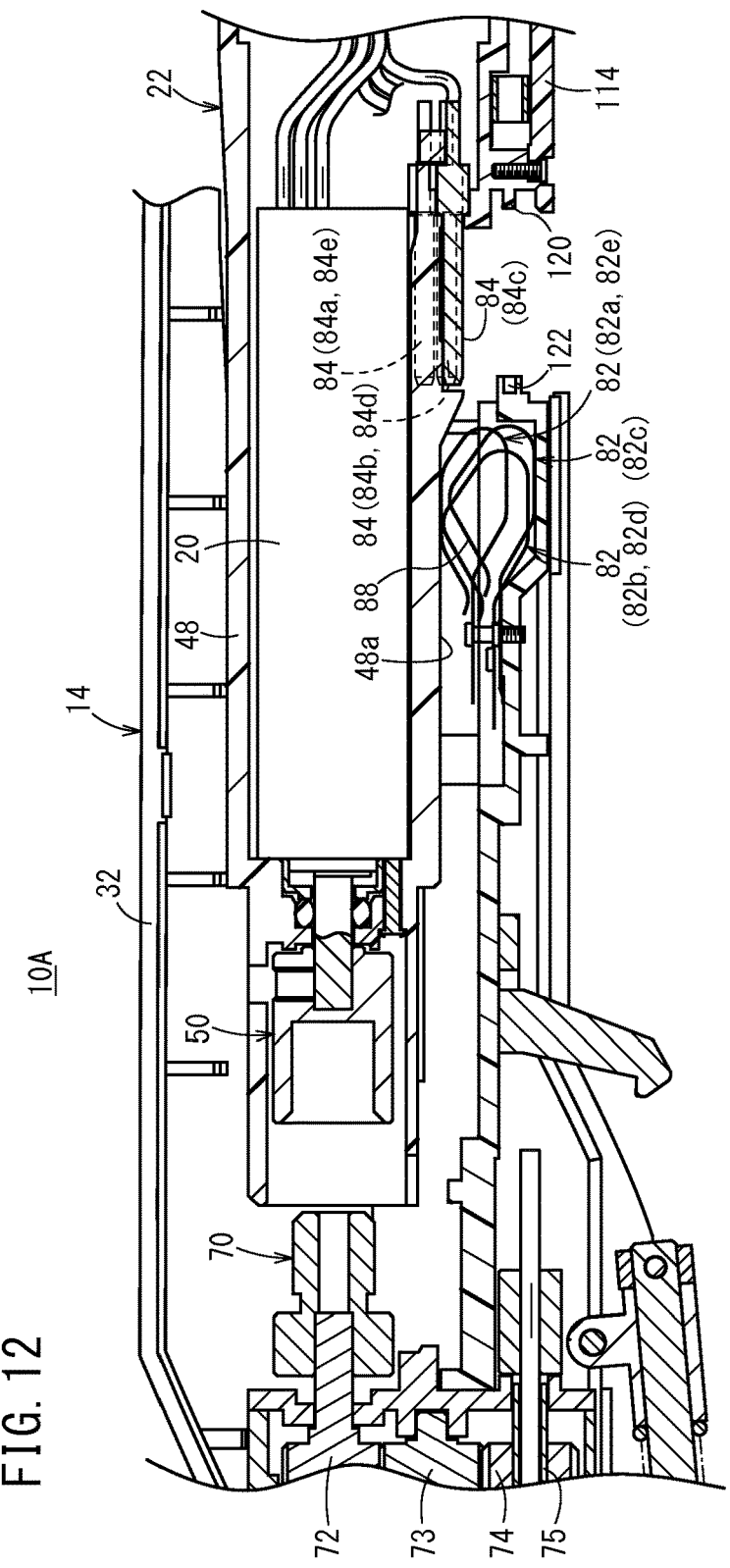
FIG. 12 is an explanatory drawing showing a condition in which the drive unit is further advanced with respect to the handle from the state shown in FIG. 11.

In addition, upon further advancement of the drive unit 22, as shown in FIG. 12, the drive coupling 50 approaches toward the driven coupling 70, and the elastic pieces 88 of the handle-side terminal members 82a to 82e begin to enter into a groove 48a (see also FIG. 9) that is formed on a lower portion of the housing 48.

Figure 13:
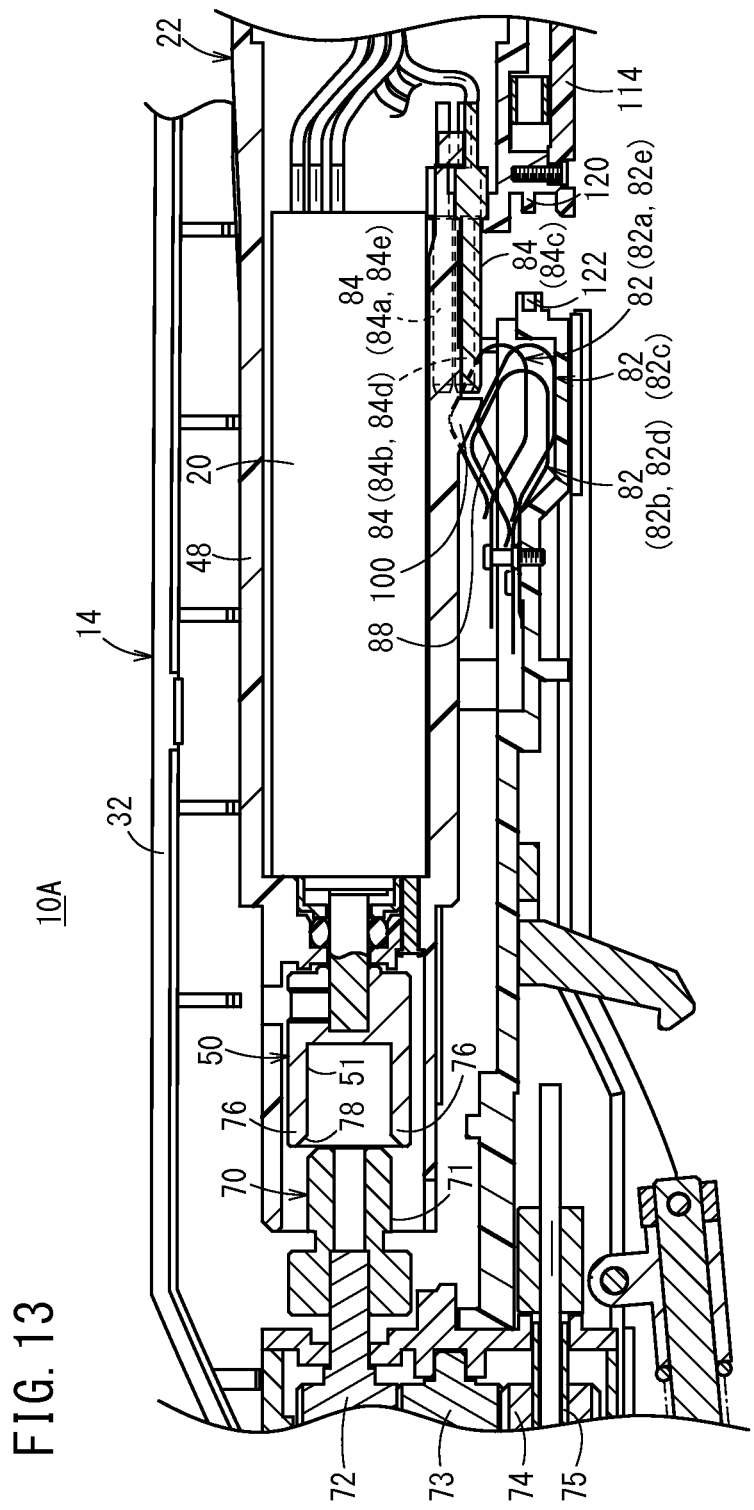
FIG. 13 is an explanatory drawing showing a condition in which the drive unit is further advanced with respect to the handle from the state shown in FIG. 12, and a distal end position of the drive coupling and a proximal end position of a driven coupling are made to coincide.

As shown in FIG. 13, upon further advancement of the drive unit 22, the distal end of the drive coupling 50 and the proximal end of the driven coupling 70 come into contact, whereupon fitting of the drive coupling 50 with the driven coupling 70 is started. In this case, since the tooth-end portions 76 of the teeth 51 of the drive coupling 50 are formed to become smaller in width toward the open side (see FIG. 6), at the time of contact between the drive coupling 50 and the driven coupling 70, although the phases of the teeth 51, 71 overlap, while the driven coupling 70 undergoes rotation, the drive coupling 50 is inserted along the tooth surfaces 76a of the tooth-end portions 76, which become narrower toward the end surfaces 76b in the axial direction. Consequently, fitting between the drive coupling 50 and the driven coupling 70 can be carried out reliably and easily. Further, since the tapered portions 78, which are tilted so as to be displaced in a radial outward direction toward the distal end side, are provided on the distal ends of the teeth 51 of the drive coupling 50, fitting of the drive coupling 50 and the driven coupling 70 can be performed more smoothly.

Further, as shown in FIG. 13, at a point in time that fitting between the drive coupling 50 and the driven coupling 70 is started, the elastic pieces 88 of the handle-side terminal members 82 are pressed and resiliently deformed downwardly by the protrusions 100 provided on the lower portion of the housing 48, and a condition is brought about in which contact with the unit-side terminal members 84 is prevented. Since the tapered lower surfaces 100a (see FIG. 9) are provided on the protrusions 100, the elastic pieces 88 of the handle-side terminal members 82 are easily deformed elastically accompanying movement of the drive unit 22. Consequently, there is no impediment to insertion of the drive unit 22.

Figure 14:
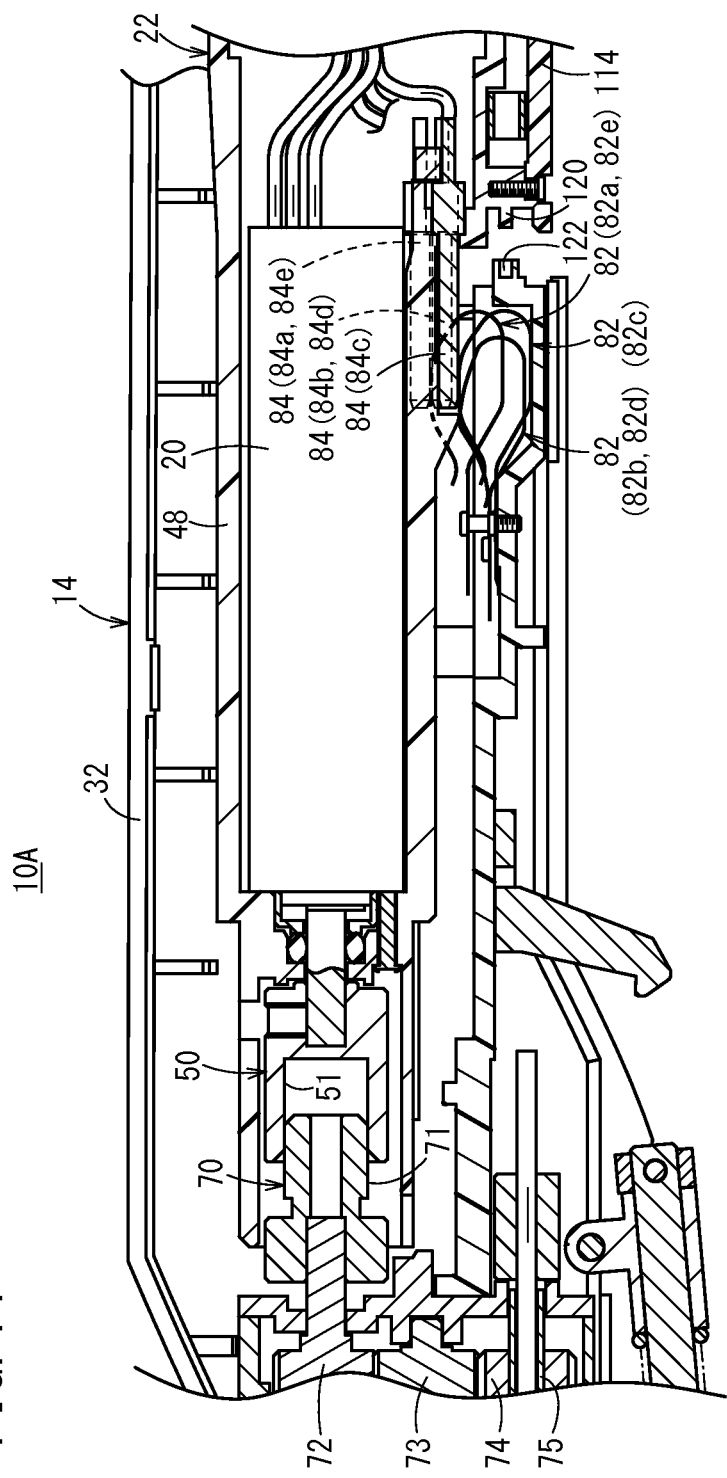
FIG. 14 is an explanatory drawing showing a condition in which the drive unit is further advanced with respect to the handle from the state shown in FIG. 13, and a connection is initiated between a switch terminal disposed on the handle and a unit-side terminal disposed on the drive unit.

As shown in FIG. 14, upon further advancement of the drive unit 22, among the handle-side terminal members 82a to 82e, the three handle-side terminal members 82a, 82c, 82e that constitute switch terminals come into contact with the three unit-side terminal members 84a, 84c, 84e that correspond therewith. At this time, the remaining two handle-side terminal members 82b, 82d that constitute detection terminals do not yet come into contact with the unit-side terminal members 84b, 84d.

Figure 15:
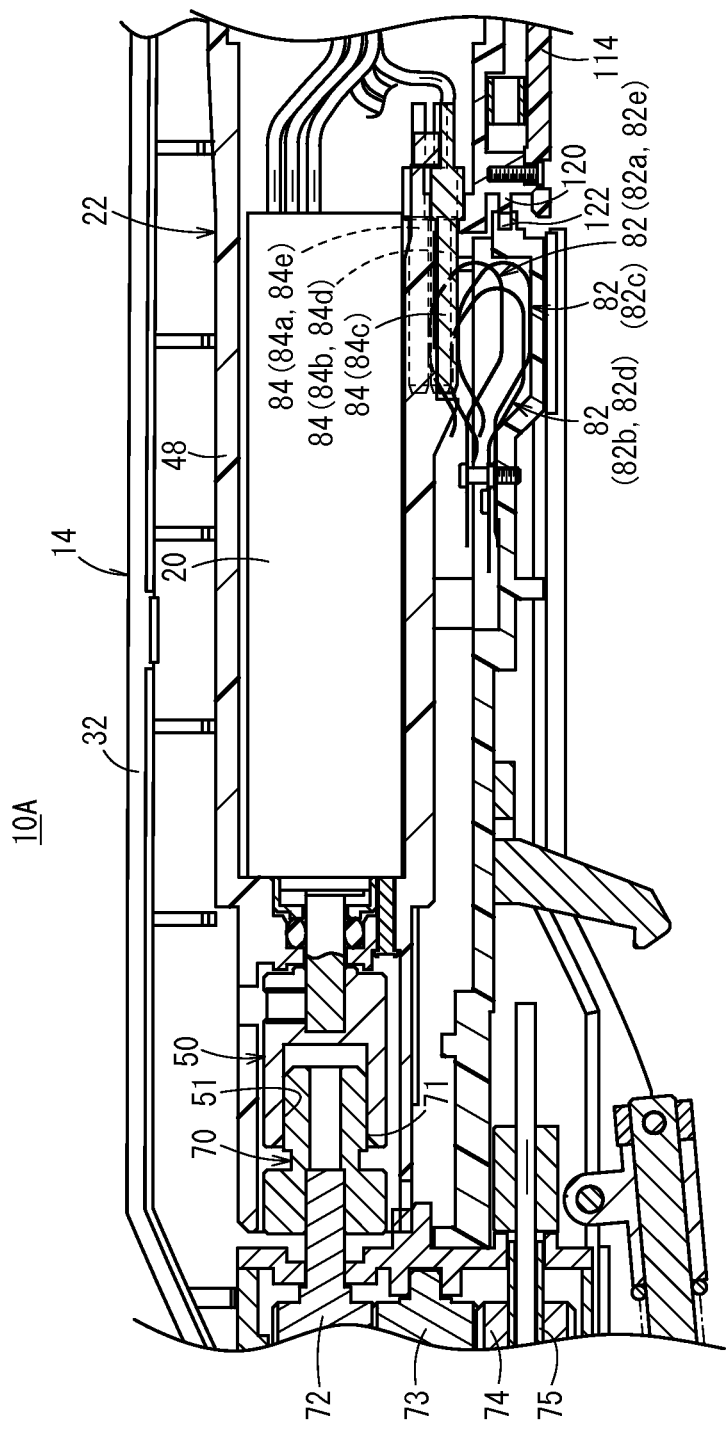
FIG. 15 is an explanatory drawing showing a condition in which the drive unit is further advanced with respect to the handle from the state shown in FIG. 14, and a connection is initiated between the detection terminal disposed on the handle and the unit-side terminal disposed on the drive unit.

In addition, as shown in FIG. 15, upon further advancement of the drive unit 22, the two handle-side terminal members 82b, 82d that constitute detection terminals come into contact with the unit-side terminal members 84b, 84d. In this manner, in the manipulator 10A, when the drive unit 22 is moved to mount the drive unit 22 with respect to the handle 14, after the handle-side terminal members 82a, 82c, 82e that constitute the switch terminals have contacted the unit-side terminal members 84a, 84c, 84e corresponding thereto, the handle-side terminal members 82b, 82d that constitute the detection terminals are placed in contact with the remaining unit-side terminal members 84b, 84d. Thereafter, the positioning pin 120 that is provided on the lower portion of the drive unit 22 (lower portion of the housing 48) starts to be fitted into the positioning hole 122 provided on the proximal end of the unit holder 86.

Figure 16A:
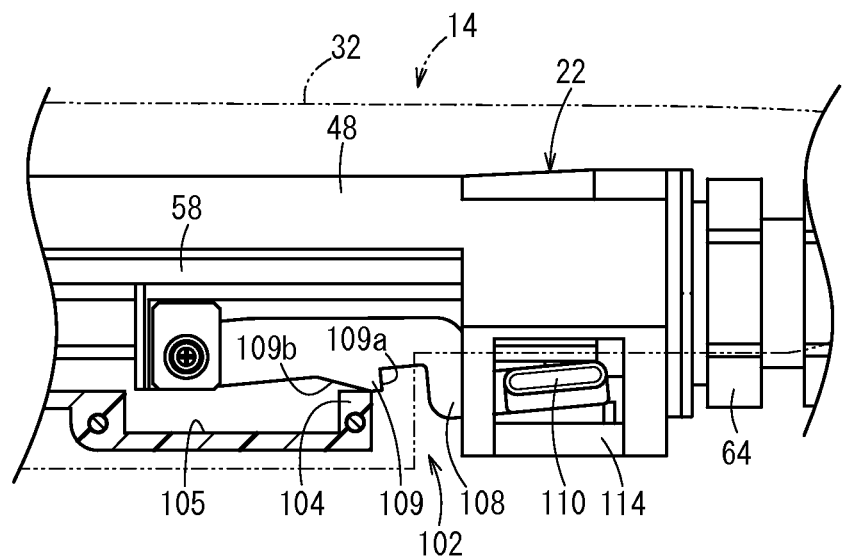
FIG. 16A is an explanatory drawing showing a condition in which an engagement pawl of a lever member rides over a latching member.
Figure 16B:
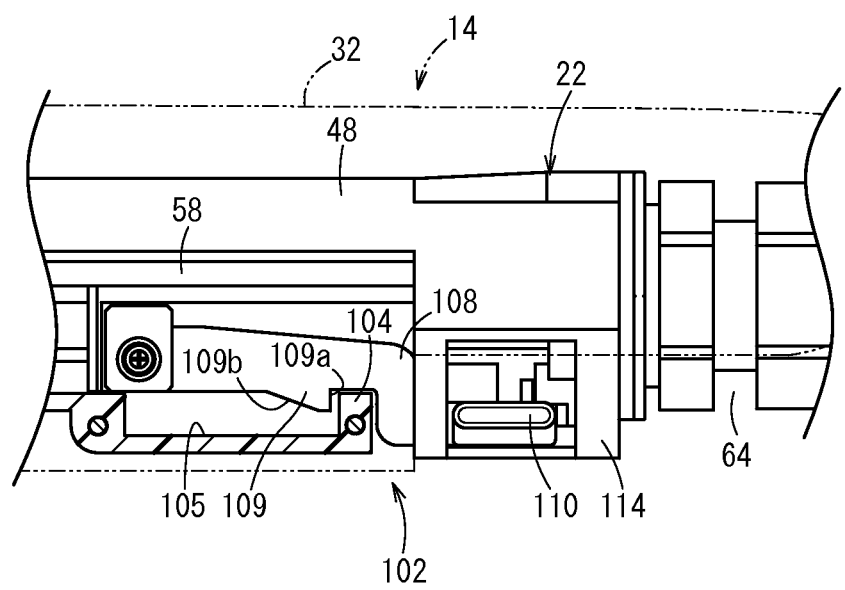
FIG. 16B is an explanatory drawing showing a condition in which the engagement pawl has surpassed the latching member and enters into an engagement groove.

On the other hand, while the handle-side terminal members 82 and the unit-side terminal members 84 come into contact, and as shown in FIG. 16A, the engagement pawls 109 of the lever members 108 ride up onto the engagement members 104. In addition, at a position in which the drive unit 22 has advanced slightly from the position (see FIG. 15) in which the handle-side terminal members 82b, 82d and the unit-side terminal members 84b, 84d begin to contact one another, as shown in FIG. 16B, the engagement pawls 109 drop off from the engagement members 104, and under the biasing action from the biasing member 112 (see FIG. 10), the lever members 108 are restored to their original positions. As a result, a condition (locked state) is brought about in which movement of the drive unit 22 in the proximal end direction relative to the handle 14 is prevented.

Moreover, at the position at which the drive unit 22 has been advanced slightly from the position where the engagement pawls 109 drop off from the engagement members 104, as shown in FIG. 4, by the distal end of the housing 48 of the drive unit 22 abutting against a portion of the handle 14 (in the illustrated example, a frame 124 that rotatably supports the gear shaft 72 to which the driven coupling 70 is fixed), the drive unit 22 is stopped. As a result, a state (attached state) is brought about in which the drive unit 22 is attached appropriately with respect to the handle 14. In the attached state, not only the guide rails 56 and the guide receiving members 58 are fitted together, but since positioning is also effected by fitting the positioning pin 120 into the positioning hole 122, a secure positional relationship between the handle 14 and the drive unit 22 is stably maintained.

In the attached state of the drive unit 22, when the rolling switch 28 is operated, the operating state of the rolling switch 28 is detected in the controller 36 through the handle-side terminal members 82a, 82c, 82e (see FIGS. 7A and 7B) and the unit-side terminal members 84a, 84c, 84e (see FIG. 8) that make up the electrical connection mechanism 80, and the controller 36 controls driving of the motor 20. The driving force of the motor 20 is transmitted to the handle 14 through the power coupling 69 that is made up from the drive coupling 50 and the driven coupling 70, and motive power is further transmitted to the distal end working unit 18 through the power transmission system in the interior of the handle 14, whereupon the distal end working unit 18 performs a predetermined operation (in the present example, a rolling operation).

To remove the drive unit 22 from the handle 14, the operation tabs 110 provided in the drive unit 22 (see FIG. 1) may be operated and pulled up with the fingers. Upon doing so, together with the lever members 108 being displaced upwardly in opposition to the elastic force of the biasing member 112, the engagement between the engagement pawls 109 and the engagement members 104 is released, and the drive unit 22 can be moved in the proximal end direction with respect to the handle 14. At this time, due to the resilient force of the elastic members 116 (see FIG. 10) in the return spring member 115, the drive unit 22 moves slightly in the proximal end direction, and therefore, it is easy to pull out the drive unit 22.

Figure 17:
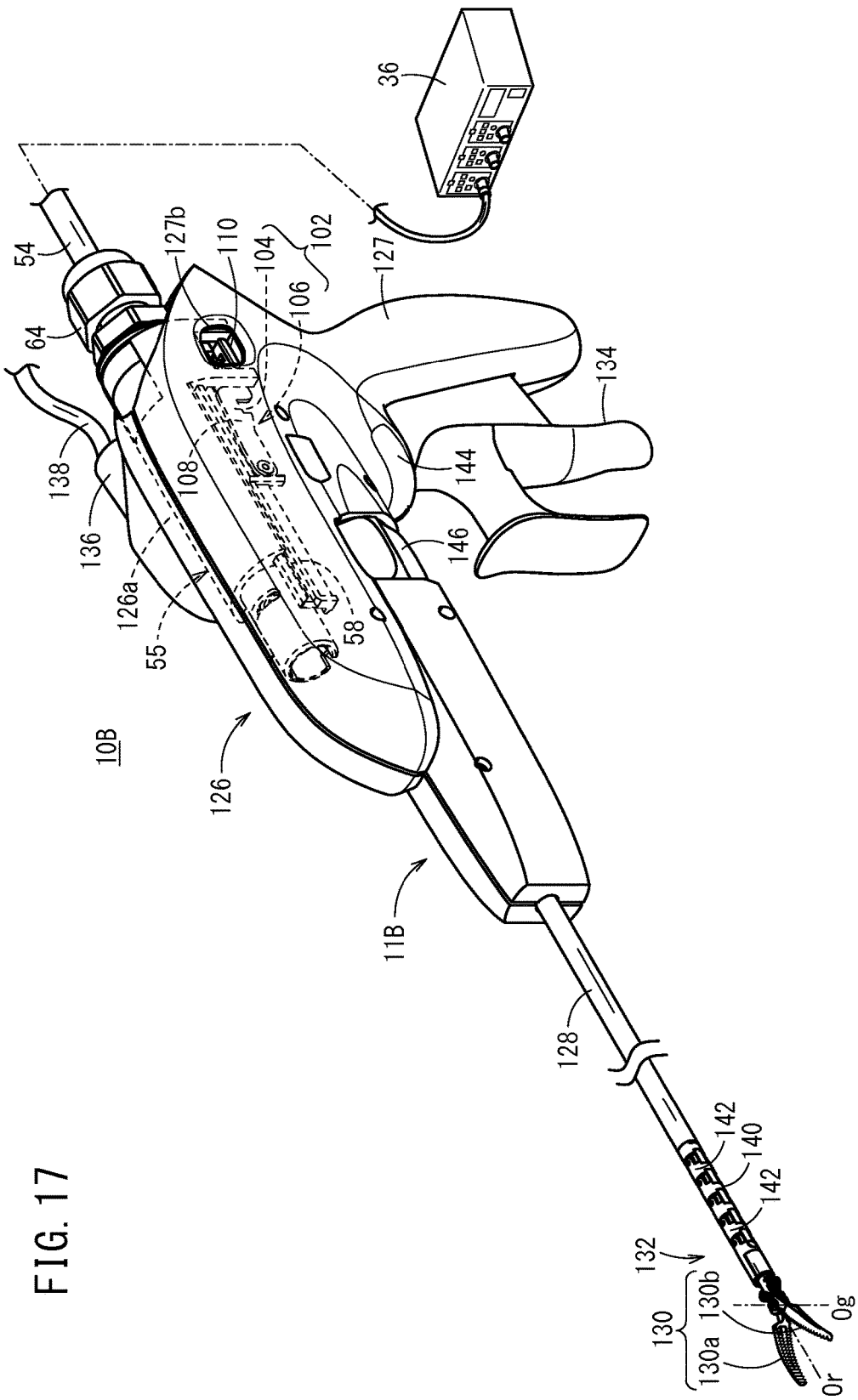
FIG. 17 is a perspective view with partial omission of a medical manipulator according to a combination of the drive unit and another form of the manipulator main body.

The drive unit 22, which is constructed as described above, can be mounted and used not only with the manipulator main body 11A, which is constituted as a needle driver, but also with a manipulator main body 11B, which is constituted as an electrosurgical scalpel, as shown in FIG. 17. In this case, by combining together the manipulator main body 11B and the drive unit 22, an electrosurgical scalpel type medical manipulator 10B (hereinafter referred to in an abbreviated form as a "manipulator 10B"), which is driven by the motor 20, is constructed.

The manipulator main body 11B comprises a handle 126 on which a plurality of input operating members are provided, a shaft 128 that extends from the handle 126, and a distal end working unit 132 disposed on a distal end of the shaft 128 and including a gripper 130 (end effector). The manipulator main body 11A shown in FIG. 1 is of an overall stick-like (rod-like) shape suitable for use as a needle driver. In contrast thereto, with the manipulator main body 11B shown in FIG. 17, a grip 127 that projects downwardly on a lower part of the handle 126 is provided, and the handle 126 is in the shape of a pistol as a whole, having a shape that is suitable for use as an electrosurgical scalpel. Further, such a pistol type handle shape also is suitable for use with scissors, a grasping implement, and a peeling implement, etc.

The gripper 130 is capable of making opening and closing movements, and serves as a portion for gripping biological tissue, and cauterizing the biological tissue by conduction of current through the tissue. The gripper 130 of the present illustrated example includes a first gripper member 130a and a second gripper member 130b, which are capable of swinging or pivoting in mutually opposite directions about an opening and closing operation axis Og. The manipulator main body 11B may be constructed as a bipolar type of electrical scalpel in which the first gripper member 130a and the second gripper member 130b are electrically energized at different polarities, or a monopolar type of electrical scalpel in which either one of the first gripper member 130a or the second gripper member 130b is electrically energized.

The opening and closing operation of the gripper 130 is carried out by mechanically transmitting the operation of a lever 134, which is provided on the handle 126, to the distal end working unit 132 through a non-illustrated opening/closing drive transmission system. More specifically, in the present illustrated example, the lever 134 is constructed as a manual operating member, and opening and closing operations of the gripper 130 are performed not by a motor drive, but by a manual drive on the basis of an operating force from the operator.

The lever 134 is disposed for displacement in forward and rearward directions with respect to the grip 127, such that when the lever 134 is pressed out forwardly relative to the grip 127, the gripper 130 opens, and when the lever 134 is drawn in rearwardly relative to the grip 127, the gripper 130 is closed. A structure may also be adopted in which the opening/closing operation of the gripper 130 is performed by a motor drive.

In the manipulator 10B in accordance with the combination of the manipulator main body 11B and the drive unit 22, a power supplying connector 136 is connected to the handle 126, whereby the manipulator 10B can be used as an electrosurgical scalpel. The power supplying connector 136 is connected to a non-illustrated high frequency power supply device through an energizing cable 138, and by the high frequency power supply device, a high frequency voltage is applied in order to electrically energize the gripper 130.

The distal end working unit 132 is capable of being tilted laterally (yaw operation) by a bending portion 140 disposed on a distal end of the shaft 128. The bending portion 140 has a plurality of joint members 142, which are coupled rotatably within a predetermined angular range to one another.

Although in a state in which the joint members 142 are aligned coaxially, the bending portion 140 exhibits a linear shape, when the adjacent joint members 142 themselves are mutually tilted, the bending portion 140 exhibits a curved shape as a whole.

The tilting operation of the distal end working unit 132 is carried out by the controller 36 controlling driving of the motor 20 based on an operation made with respect to a tilting switch 144 provided on the handle 126, and by mechanically transmitting the driving force of the motor 20 to the distal end working unit 132 through the handle 126 and the shaft 128. More specifically, in the present illustrated example, the tilting switch 144 is constructed as an electrical operating member, and the tilting operation of the distal end working unit 132 is performed by a motor drive.

The distal end working unit 132, at a portion thereof located more toward the distal end side than the bending portion 140, is capable of executing a rolling operation about the roll axis Or. The rolling operation is carried out by mechanically transmitting a rotating operation made with respect to a rotating knob 146 (input operating member), which is provided on the handle 126, to the distal end working unit 132 through a non-illustrated rolling drive transmission system. More specifically, in the present illustrated example, the rotating knob 146 is constructed as a manual operating member, and the rolling operation of the distal end working unit 132 is performed not by a motor drive, but by a manual drive on the basis of an operating force from the operator. A structure may also be adopted in which the rolling operation of the distal end working unit 132 is performed by a motor drive.

On an upper end side of the handle 126, a mounting hole 126a is provided, which opens rearwardly. The drive unit 22 is inserted into the mounting hole 126a, and thus can be mounted with respect to the handle 126. More specifically, the drive unit 22 is capable of being attached to and detached from the proximal end side of the handle 126. In a state in which the drive unit 22 is mounted in the handle 126, so that operating tabs 110, which are disposed on the drive unit 22, can be touched and operated by the user, the operating tabs 110 protrude through openings 127b provided on side surfaces on left and right sides of the handle 126.

Although omitted from illustration in FIG. 17, guide rails 56 (see FIG. 5) are provided on the handle 126, which are similar to those of the handle 14 in the manipulator main body 11A. Consequently, under a guiding action of a guide mechanism 55 made up from the guide rails 56 and the guide receiving members 58, the drive unit 22 can move smoothly relative to the handle 126, and the drive unit 22 can be mounted easily and reliably at an accurate positional relationship with respect to the handle 126.

Although omitted from illustration in FIG. 17, a driven coupling 70 (see FIG. 4) is provided in the handle 126, which is similar to that of the handle 14 in the manipulator main body 11A. Consequently, in a state in which the drive unit 22 is mounted with respect to the handle 126, by engagement of the drive coupling 50 and the driven coupling 70, a driving force of the motor 20 can be transmitted reliably to the handle 126.

Although omitted from illustration in FIG. 17, a plurality of handle-side terminal members 82 (see FIG. 4) are provided in the handle 126, which are similar to those of the handle 14 in the manipulator main body 11A. Consequently, in a state in which the drive unit 22 is mounted with respect to the handle 126, by the plural handle-side terminal members 82 being placed in contact with the plural unit-side terminal members 84, an operating state of the tilting switch 144 can be detected reliably by the controller 36, and the controller 36 can appropriately control driving of the motor 20.

On the handle 126, similar to the handle 14 shown in FIG. 1 and the like, engagement members 104 are provided that are capable of engaging with engagement pawls 109 of the lever members 108 disposed on the drive unit 22. Accordingly, together with attachment of the drive unit 22 with respect to the handle 126, a condition (locked state) is brought about in which movement of the drive unit 22 in the proximal end direction relative to the handle 126 is prevented.

In this manner, the drive unit 22 can be attached and detached with respect to the manipulator main bodies 11A, 11B (forceps portions) having different functions and shapes, and in the attached state, transmission of a driving force of the motor 20 to the handles 14, 126, electrical connections between the handles 14, 126 and the drive unit 22, and preventing the drive unit 22 from moving with respect to the handles 14, 126 can reliably be achieved.

The form of the manipulator main bodies 11A, 11B, which enable attachment and detachment of the drive unit 22, is not limited to the two forms (needle driver, electrosurgical scalpel) described above, and forms having other different functions and shapes, for example, scissors, a grasping forceps, or the like, may be provided. In addition, a suction device, a cleaning device, an energy device, etc., may be provided.

As described above, with the medical manipulators 10A, 10B according to the present embodiment, by providing the guide mechanism 55 (see FIG. 5), which is made up from the guide rails 56 and the guide receiving members 58, the drive unit 22 can be attached smoothly and easily at an appropriate positional relationship with respect to the handles 14, 126. Further, by providing the power coupling 69 (see FIG. 4), which is made up from the drive coupling 50 and the driven coupling 70, in a state in which the drive unit 22 is attached with respect to the handles 14, 126, based on the driving force of the motor 20, the distal end working unit 18 can be operated reliably. Furthermore, by providing the electrical connection mechanism 80 (see FIG. 4) made up from the handle-side terminal members 82 and the unit-side terminal members 84, the rolling switch 28 operating condition can be detected in the controller 36, and driving of the motor 20 can appropriately be controlled.

Consequently, by being equipped with the guide mechanism 55, the power coupling 69, and the electrical connection mechanism 80 in the foregoing manner, the drive unit 22 can be mounted easily and reliably with respect to handles 14, 126 having different shapes and functions, and together therewith, based on an operation of an input operating member (rolling switch 28, tilting switch 144) disposed on the handles 14, 126, the motor 20 can be driven, and the distal end working unit 18 can be operated by the driving force thereof.

In the case of the present embodiment, a movement direction of the drive unit 22 when the drive unit 22 is attached and detached with respect to the handles 14, 126 may be a lengthwise direction of the drive unit 22 and a longitudinal (forward/rearward) direction of the handles 14, 126. According to such a configuration, in a state in which the drive unit 22 is attached to the handles 14, 126, the medical manipulators 10A, 10B can be constructed in a compact manner, without the drive unit 22 projecting out significantly from the handles 14, 126.

In the present embodiment, the drive unit 22 is capable of attachment and detachment from a side that is opposite to the side on which the shafts 16, 128 are provided in the handles 14, 126. In accordance with this configuration, since the shafts 16, 128 do not become an obstruction during attachment and detachment of the drive unit 22, the operation of attaching and detaching the drive unit 22 is facilitated.

In the case of the present embodiment, the guide mechanism 55 includes the guide rails 56 disposed on the handles 14, 126, and the guide receiving members 58 disposed on the drive unit 22. According to this configuration, when the drive unit 22 is attached to the handles 14, 126, since the guide receiving members 58 provided on the drive unit 22 slide along the guide rails 56 provided on the handles 14, 126, the attachment operation of the drive unit 22 can be carried out smoothly and easily. Further, upon attachment thereof, the drive unit 22 can be guided appropriately to an exact mounting position.

In the present embodiment, in a state in which the drive unit 22 is mounted with respect to the handles 14, 126, because the drive coupling 50 is fitted coaxially with the driven coupling 70, the driving force from the motor 20 can be transmitted efficiently to the driven coupling 70 from the drive coupling 50.

In the present embodiment, at the time of contact between the drive coupling 50 and the driven coupling 70, although the phases of the teeth 51, 71 overlap, accompanying relative rotation between the drive coupling 50 and the driven coupling 70, both of the couplings 50, 70 are fitted together along the tooth surfaces 76*a* (see FIG. 6) of the tooth-end portions 76, which become narrower toward the end surfaces 76*b* in the axial direction. Consequently, fitting between the drive coupling 50 and the driven coupling 70 can be carried out reliably and easily.

In the case of the present embodiment, as to the drive coupling 50 and the driven coupling 70, the tooth-end portions 76, which become narrower toward the end surfaces 76*b* thereof in the axial direction, are provided on the drive coupling 50. Thus, with respect to either one of the handles 14, 126 having different functions and shapes, fitting between the drive coupling 50 and the driven coupling 70 can easily and reliably be carried out upon attachment of the drive unit 22.

In the case of the present embodiment, in the drive coupling 50 in which the tooth-end portions 76 are provided, a curve of the tooth shape is formed as an involute curve. By this configuration, since the tooth-end portions 76 become thinner continuously in the axial direction from the tooth shape, which is formed by an involute curve, fitting between the drive coupling 50 and the driven coupling 70 can be carried out more smoothly.

In the case of the present embodiment, accompanying relative movement of the drive unit 22 with respect to the handles 14, 126 when the drive unit 22 is attached and detached with respect to the handles 14, 126, the unit-side terminal members 84 slide while in abutment with the handle-side terminal members 82. In accordance with such a configuration, upon attachment and detachment of the drive unit 22 with respect to the handles 14, 126, the handle-side terminal members 82 and the unit-side terminal members 84 rub against each other, and at the portions subjected to such mutual rubbing, an effect (refreshing effect) by which the electrical contact point is activated can be obtained. Consequently, for example, with respect to the drive unit 22 or the manipulator main bodies 11A, 11B, even if corrosion in the handle-side terminal members 82 or the unit-side terminal members 84 occurs by performing a sterilization treatment (autoclave sterilization, etc.) using high-pressure steam, or even if foreign matter is deposited thereon or adhered thereto, the electrical connection can suitably be assured as a result of the refreshing effect upon attachment and detachment of the drive unit 22.

In the case of the present embodiment, the handle-side terminal members 82 include the elastic pieces 88 (refer to FIG. 7A) that are capable of being deformed elastically, and in the attached state, the handle-side terminal members 82 and the unit-side terminal members 84 come into contact at portions of the elastic pieces 88. In accordance with this configuration, since the handle-side terminal members 82 and the unit-side terminal members 84 are held together in intimate contact in a pressed condition by the elastic force of the elastic pieces 88, conduction between both members is further improved. Together therewith, upon attachment of the drive unit 22, due to the handle-side terminal members 82 and the unit-side terminal members 84 rubbing against one another mutually, it is easy for the refreshing effect to be more effectively exhibited.

In the present embodiment, in a state in which the drive unit 22 is attached to the handles 14, 126, the handle-side terminal members 82*b*, 82*d* that constitute detection terminals come into contact with the unit-side terminal members 84*b*, 84*d*, which are disposed on the drive unit 22 so as to correspond to the handle-side terminal members 82*b*, 82*d*. According to such a configuration, whether or not the drive unit 22 has been attached with respect to the handles 14, 126 can be detected easily.

In the present embodiment, since the motor 20 is housed in an airtight manner inside the housing 48 (refer to FIG. 4), even in the case that the drive unit 22 is subjected to sterilization under a high pressure steam atmosphere (for example, autoclave sterilization), the motor 20 remains protected within the housing 48. More specifically, since the drive unit 22 includes a structure that can withstand corrosion by the steam in the sterilization treatment under a high-pressure steam atmosphere, damage to the motor 20 due to the sterilization process can be prevented, and durability can be enhanced.

With the medical manipulators 10A, 10B described above, a configuration is provided in which the operating state of the rolling switch 28 or the tilting switch 144 is detected in the controller 36 through the electrical connection mechanism 80. In a modification of the medical manipulators 10A, 10B, movement of the rolling switch 28 or the tilting switch 144 may be transmitted to the drive unit 22 through a link mechanism.

In this case, an electrical switch, for example, a tact switch or the like, is disposed in the drive unit 22. An airtight and liquidtight condition with the exterior is secured by covering the electrical switch with a cover body made of silicone rubber, for example. When the rolling switch 28 or the tilting switch 144 is operated, through the link mechanism, movement due to the operation thereof is converted into a movement for pressing the electrical switch provided in the drive unit 22. According to such a configuration, it is possible to eliminate the presence of an electrical switch on the handle 14.

Figure 18A:
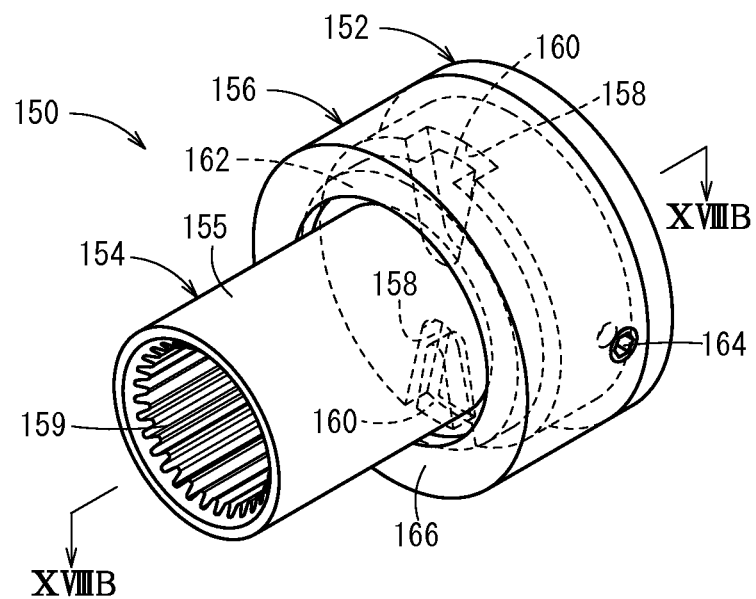
FIG. 18A is a perspective view of a drive coupling according to a modification.
Figure 18B:
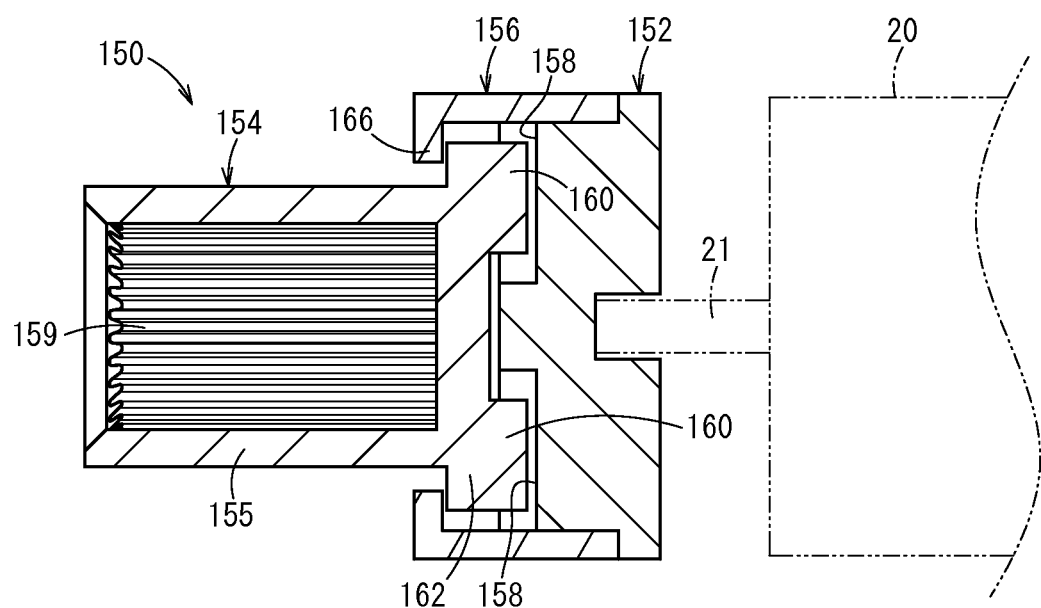
FIG. 18B is a cross-sectional view taken along line XVIIIB-XVIIIB of FIG. 18A.
Figure 19:
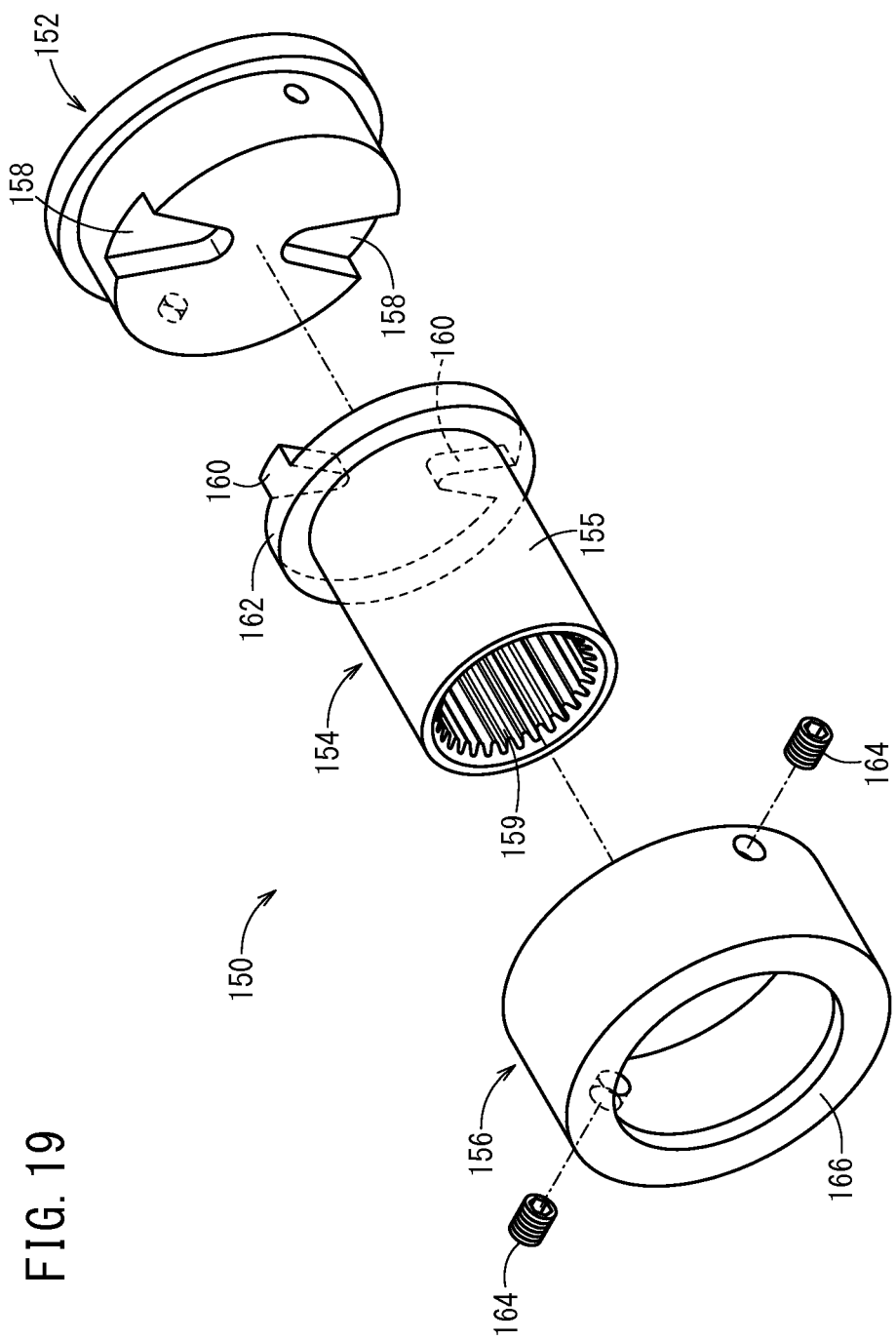
FIG. 19 is an exploded perspective view of the drive coupling shown in FIG. 18A.

In the above-described drive unit 22, instead of the drive coupling 50, a drive coupling 150 (drive member) may be adopted according to the modification shown in FIGS. 18A to 19. FIG. 18A is a perspective view of the drive coupling 150. FIG. 18B is a cross-sectional view taken along line XVIIIB-XVIIIB of FIG. 18A. FIG. 19 is an exploded perspective view of the drive coupling 150.

The drive coupling 150 includes a coupling base member 152, a coupling main body portion 154, and a retaining member 156. The coupling base member 152 is fixed to the output shaft 21 of the motor 20, and is driven rotatably by the motor 20. Engagement recesses 158 are disposed on a distal end surface (a surface on a side opposite to the side on which the output shaft 21 is fixed) of the coupling base member 152. In the coupling base member 152 of the illustrated example, two engagement recesses 158 are provided. The two engagement recesses 158 are disposed on opposite sides from each other about an axial center of the coupling base member 152. The respective engagement recesses 158 of the illustrated example extend in radial directions of the coupling base member 152. One engagement recess 158 may be provided, or three or more of such engagement recesses 158 may be provided at intervals in the circumferential direction.

The coupling main body portion 154 is a member that receives a rotational force from the coupling base member 152 and rotates together with the coupling base member 152. In the present illustrated example, the coupling main body portion 154 is of a hollow bottomed cylindrical shape. On an inner circumferential part of the coupling main body portion 154 (an inner circumferential part of a cylindrical portion 155 of the coupling main body portion 154), a plurality of circumferentially arrayed teeth 159 are provided. The coupling main body portion 154 and the driven coupling 70 are capable of being fitted together in a state in which the teeth 159 of the coupling main body portion 154 and the teeth 71 of the driven coupling 70 (see FIG. 4) are enmeshed. Further, the respective teeth 159 of the coupling main body portion 154, in the same manner as the respective teeth 51 in the drive coupling 50 shown in FIG. 6, may have tooth-end portions that narrow in width toward the distal end direction, or may not have such tooth-end portions (the width thereof may be constant).

Engagement protrusions 160, which project toward the coupling base member 152, are provided on the proximal end of the coupling main body portion 154. More specifically, in the illustrated example, a flange 162 that projects radially-outwardly is disposed on the proximal end of the coupling main body portion 154, and the engagement protrusions 160 are disposed on a rear surface of the flange 162.

With the coupling main body portion 154 of the illustrated example, two of such engagement protrusions 160 are provided. The engagement protrusions 160 extend along the diametrical direction of the coupling main body portion 154. The two engagement protrusions 160 are disposed on opposite sides from each other about an axial center of the coupling main body portion 154. One engagement protrusion 160 may be provided, or three or more of such engagement protrusions 160 may be provided at intervals in the circumferential direction.

The engagement protrusions 160 provided on the coupling main body portion 154 are smaller than the engagement recesses 158 provided on the coupling base member 152. A slight gap (amount of play) exists between the engagement protrusions 160 and the engagement recesses 158. Therefore, the coupling main body portion 154, on an inner surface thereof perpendicular to the axial direction of the drive coupling 150, is capable of relative displacement with respect to the coupling base member 152. Stated otherwise, the coupling main body portion 154 is capable of relative displacement with respect to the coupling base member 152, in a direction perpendicular to the axial direction of the drive coupling 150.

The retaining member 156 is fixed to the coupling base member 152. Although the retaining member 156 may be fixed by a fixing part 164 (screw) with respect to the coupling base member 152, the retaining member 156 may be fixed to the coupling base member 152 by another joining means (e.g., an adhesive or the like). The retaining member 156 retains the coupling main body portion 154 while permitting relative displacement of the coupling main body portion 154 with respect to the coupling base member 152.

The retaining member 156 of the present illustrated example is constituted in the form of a hollow cylinder, and an inwardly projecting member 166, which projects inwardly, is disposed on the distal end thereof. The inwardly projecting member 166 may extend once around (360°) in the circumferential direction as in the illustrated example, or may be disposed partially therearound in the circumferential direction. The flange 162 that is provided on the coupling main body portion 154 is arranged on an inner side of the retaining member 156. The inner diameter of the inwardly projecting member 166 is smaller than the outer diameter of the flange 162 provided on the coupling main body portion 154. Consequently, through engagement between the inwardly projecting member 166 and the flange 162, pulling out of the coupling main body portion 154 from the retaining member 156 is prevented.

The inner diameter of the inwardly projecting member 166 is greater than the outer diameter of the cylindrical portion 155 of the coupling main body portion 154. A slight gap (amount of play) exists between the inside edge of the inwardly projecting member 166 and the outer circumferential surface of the cylindrical portion 155. Therefore, the coupling main body portion 154 is capable of being displaced, only by the portion of the gap, with respect to the coupling base member 152.

In accordance with the drive coupling 150 that is configured in the above-described manner, the coupling main body portion 154 can be displaced relative to the coupling base member 152. Therefore, when the drive coupling 150 and the driven coupling 70 are engaged, axial matching of the coupling main body portion 154 and the driven coupling 70 can be performed automatically. More specifically, the coupling main body portion 154 can be displaced so as to follow the driven coupling 70, whereby the coupling main body portion 154 can automatically be aligned (centered) therewith. Consequently, resistance accompanying power transmission from the drive coupling 150 to the driven coupling 70 can be reduced.

Further, by providing the drive coupling 150 with the retaining member 156, without inhibiting the alignment function of the coupling main body portion 154, the coupling base member 152 and the coupling main body portion 154 can be coupled together to enable power transmission therebetween.

Instead of the above configuration, the engagement recesses 158 may be disposed on the coupling main body portion 154, and the engagement protrusions 160 may be disposed on the coupling base member 152.

The structural configuration of the drive coupling 150 may be applied to the driven coupling 70 shown in FIG. 4. In this case, the modification of the driven coupling 70 includes respective elements corresponding to the coupling base member 152, the coupling main body portion 154, and the retaining member 156 on the drive coupling 150. According to such a modification of the driven coupling 70 as well, when fitted to the drive coupling 50 or the drive coupling 150, an automatic centering function can be exhibited.

In the medical manipulators 10A, 10B described above, instead of the electrical connection mechanism 80 (see FIG. 4), an electrical connection mechanism of a different structure that offers the same functions or operations may be adopted. Accordingly, for example, an electrical connection mechanism 168 according to a first modification shown in FIGS. 20A and 20B, or an electrical connection mechanism 180 according to a second modification shown in FIGS. 21A and 21B may be adopted. FIGS. 20A to 21B schematically illustrate respective constituent elements.

Figure 20A:
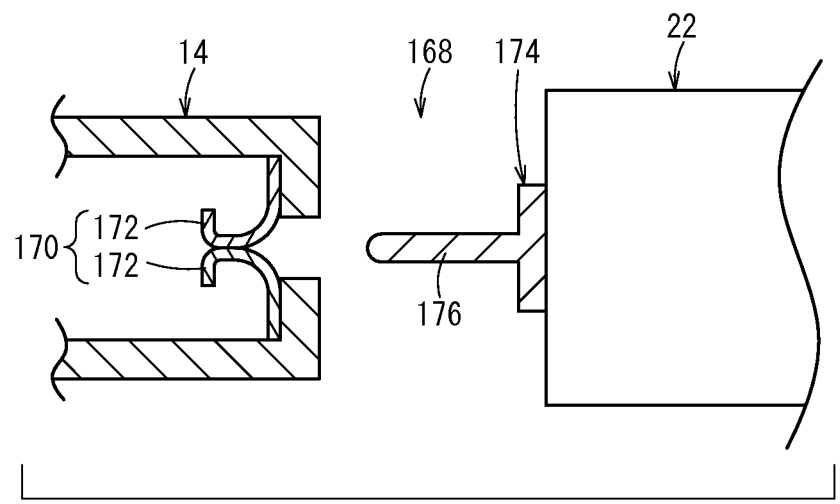
FIG. 20A is a schematic descriptive illustration of an electrical connection mechanism according to a first modification.
Figure 20B:
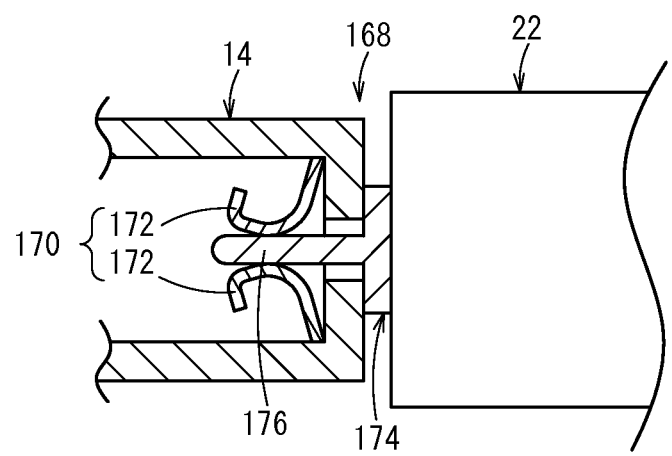
FIG. 20B is a schematic descriptive illustration showing a connected state of the electrical connection mechanism according to the first modification.

As shown in FIGS. 20A and 20B, the electrical connection mechanism 168 according to the first modification includes handle-side terminal members 170 provided on the handle 14, and unit-side terminal members 174 provided on the drive unit 22. Plural handle-side terminal members 170 are provided, having functions corresponding to those of the handle-side terminal members 82 shown in FIGS. 7A and 7B. The respective handle-side terminal members 170 are constituted from a pair of terminal pieces 172. The terminal pieces 172 are made from an electrically conductive material, and are constituted from elastically deformable plate-like members, which are bent in the illustrated shapes.

Plural unit-side terminal members 174 are provided, having functions corresponding to those of the unit-side terminal members 84 shown in FIGS. 8, 9, and the like. The respective unit-side terminal members 174 include contact members 176, which can be inserted between the pair of terminal pieces 172.

As shown in FIG. 20B, in a state in which the drive unit 22 is attached with respect to the handle 14, the contact members 176 of the unit-side terminal members 174 are inserted between the pairs of terminal pieces 172 in the handle-side terminal members 170.

When the drive unit 22 is attached and detached with respect to the handle 14, accompanying relative movement of the drive unit 22 with respect to the handle 14, the unit-side terminal members 174 slide while in abutment with the handle-side terminal members 170. The pairs of terminal pieces 172 are deformed elastically in directions away from each other accompanying insertion of the contact members 176.

Consequently, in accordance with the configuration of the electrical connection mechanism 168 according to the first modification, upon attachment and detachment of the drive unit 22 with respect to the handle 14, the handle-side terminal members 170 and the unit-side terminal members 174 rub against each other. In addition, at the portions subjected to such mutual rubbing, an effect (refreshing effect) by which the electrical contact point is activated can be obtained.

The configurations of the handle-side terminal members 170 and the unit-side terminal members 174 shown in FIGS. 20A and 20B may be switched with each other. More specifically, the modification of the handle-side terminal members 170 may be constructed in the same shape as the unit-side terminal members 174, and the modification of the unit-side terminal members 174 may be constructed in the same shape as the handle-side terminal members 170.

Figure 21A:
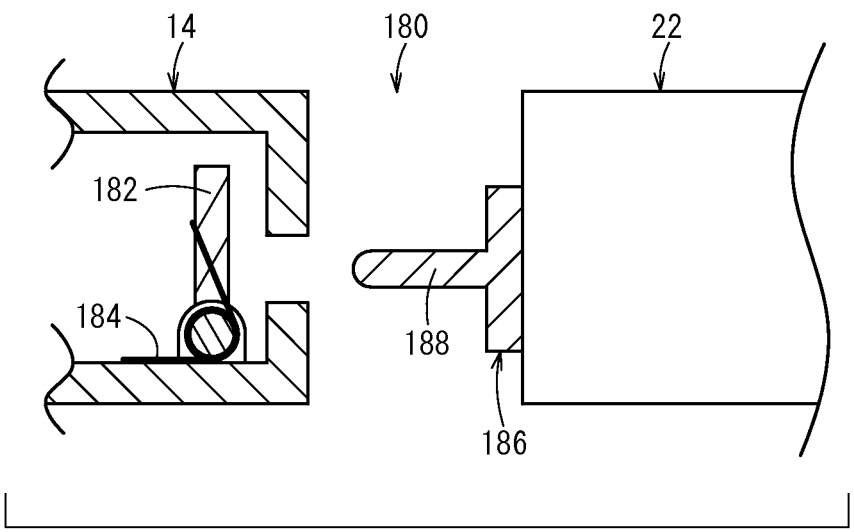
FIG. 21A is a schematic descriptive illustration of an electrical connection mechanism according to a second modification.
Figure 21B:
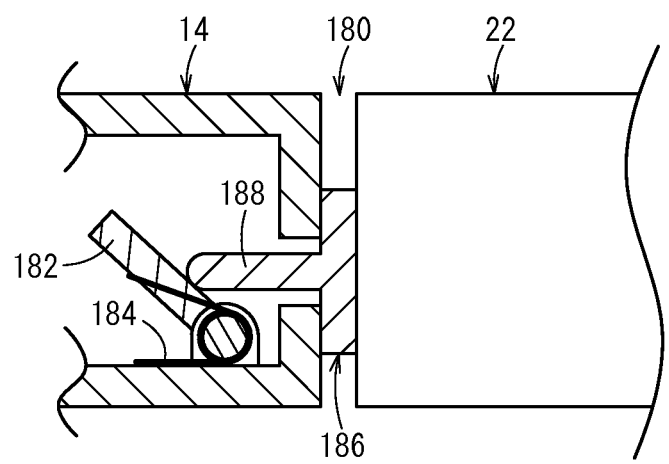
FIG. 21B is a schematic descriptive illustration showing a connected state of the electrical connection mechanism according to the second modification.

As shown in FIGS. 21A and 21B, the electrical connection mechanism 180 according to the second modification includes handle-side terminal members 182 provided on the handle 14, and unit-side terminal members 186 provided on the drive unit 22.

The plural handle-side terminal members 182 are provided, having functions corresponding to those of the handle-side terminal members 82 shown in FIGS. 7A, 7B, and the like. The respective handle-side terminal members 182 are constituted from an electrically conductive material. The respective handle-side terminal members 182 are capable of swinging forward and backward with respect to the handle 14, and by way of biasing members 184 (torsion springs in the illustrated example), are biased elastically in an upright direction. The biasing members 184 may also be constituted from coil springs, plate springs, or other elastic bodies.

The plural unit-side terminal members 186 are provided, having functions corresponding to those of the unit-side terminal members 84 shown in FIGS. 8, 9, and the like. The respective unit-side terminal members 186 include contact members 188, which are capable of pressing against the handle-side terminal members 182.

As shown in FIG. 21B, in a state in which the drive unit 22 is attached with respect to the handle 14, the contact members 188 of the unit-side terminal members 186 come into abutment with the handle-side terminal members 182. At this time, the handle-side terminal members 182 are pressed by the contact members 188 of the unit-side terminal members 186, and a condition is brought about in which the handle-side terminal members 182 are tilted forward by a predetermined angle in opposition to the biasing force (elastic force) of the biasing members 184.

With the electrical connection mechanism 180, when the drive unit 22 is attached and detached with respect to the handle 14, accompanying relative movement of the drive unit 22 with respect to the handle 14, the unit-side terminal members 186 slide while in abutment with the handle-side terminal members 182. Consequently, in accordance with the configuration of the electrical connection mechanism 180 according to the second modification, upon attachment and detachment of the drive unit 22 with respect to the handle 14, the handle-side terminal members 182 and the unit-side terminal members 186 rub against each other. In addition, at the portions subjected to such mutual rubbing, an effect (refreshing effect) by which the electrical contact point is activated can be obtained.

The configurations of the handle-side terminal members 182 and the unit-side terminal members 186 shown in FIGS. 21A and 21B may be switched with each other. More specifically, the modification of the handle-side terminal members 182 may be constructed in the same shape as the unit-side terminal members 186, and the modification of the unit-side terminal members 186 may be constructed in the same shape as the handle-side terminal members 182.

Figure 22A:
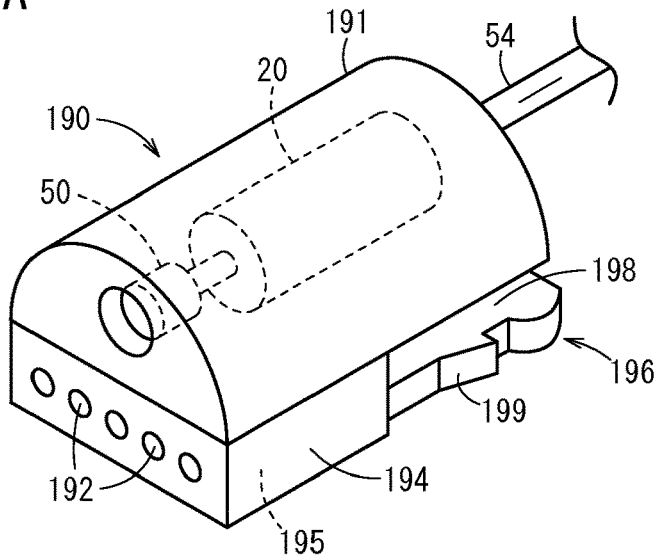
FIG. 22A is a perspective view of a drive unit according to a modification.
Figure 22B:
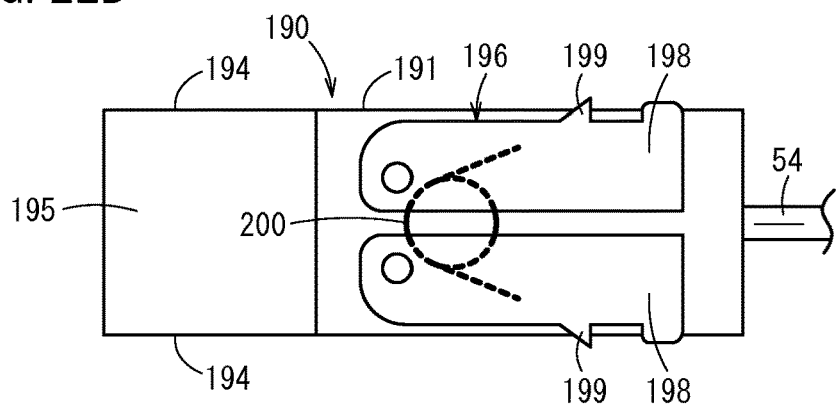
FIG. 22B is a view as seen from below of the drive unit shown in FIG. 22A.
Figure 22C:
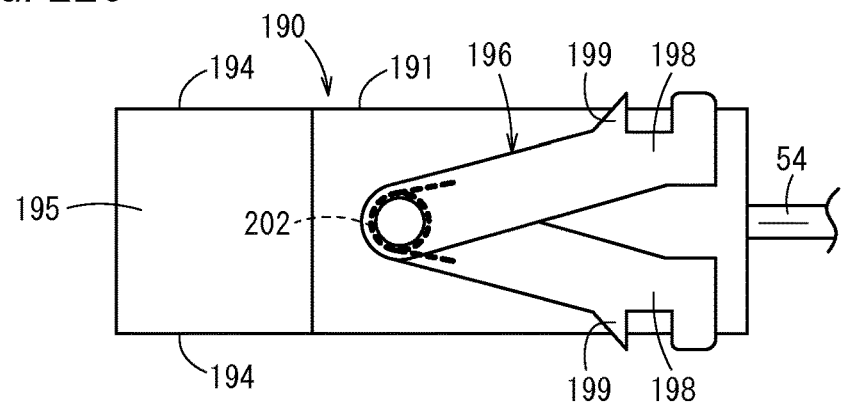
FIG. 22C is a view showing a structural example in which an arrangement of the lever member is changed.

Instead of the above-described drive unit 22, a drive unit 190 according to the modification shown in FIGS. 22A to 22C may be adopted. With the drive unit 190, instead of the unit-side terminal members 84 (see FIG. 8), unit-side terminal members 192 are disposed at intervals laterally on the distal end of the drive unit 190. In this case, in the handle 14 in which the drive unit 190 is mounted, instead of the handle-side terminal members 82 (see FIGS. 7A and 7B), non-illustrated handle-side terminal members are disposed at suitable positions on the handle 14. The unit-side terminal members 192 may also be disposed at vertical as well as lateral intervals.

In the case of the drive unit 190, both left and right side surfaces 194 and a bottom surface 195 function as guide surfaces when the drive unit 190 is attached to the handle 14. Consequently, the guide receiving members 58 provided on the drive unit 22 (see FIG. 3) are not provided on the drive unit 190, and with the handle 14, the guide rails 56 are unnecessary.

FIG. 22B is a view as seen from below of the drive unit 190. A lever device 196, which is provided on the drive unit 190, includes a pair of lever members 198, which are capable of pivoting laterally in a housing 191. The (pair of) two lever members 198 are biased elastically at all times outwardly by a biasing member 200 (a torsion spring in the illustrated example). Engagement pawls 199 are formed to project on outer side portions of the respective lever members 198. Two biasing members 200 may be provided, and the pair of lever members 198 may be biased individually by the two biasing members 200. Only one of the lever members 198 may be provided. The biasing members 200 may also be constituted from coil springs, plate springs, or other elastic bodies.

As shown in FIG. 22C, the (pair of) two lever members 198 may be partially overlapped vertically, and may be disposed so as to be swingable on the same axis. In FIG. 22C, the lever members 198 are biased outwardly by a single biasing member 202. However, two biasing members 202 may be provided, and the lever members 198 may be biased outwardly individually by the two biasing members 202. The biasing member 202 may also be constituted from a coil spring, a plate spring, or another elastic body.

Figure 23A:
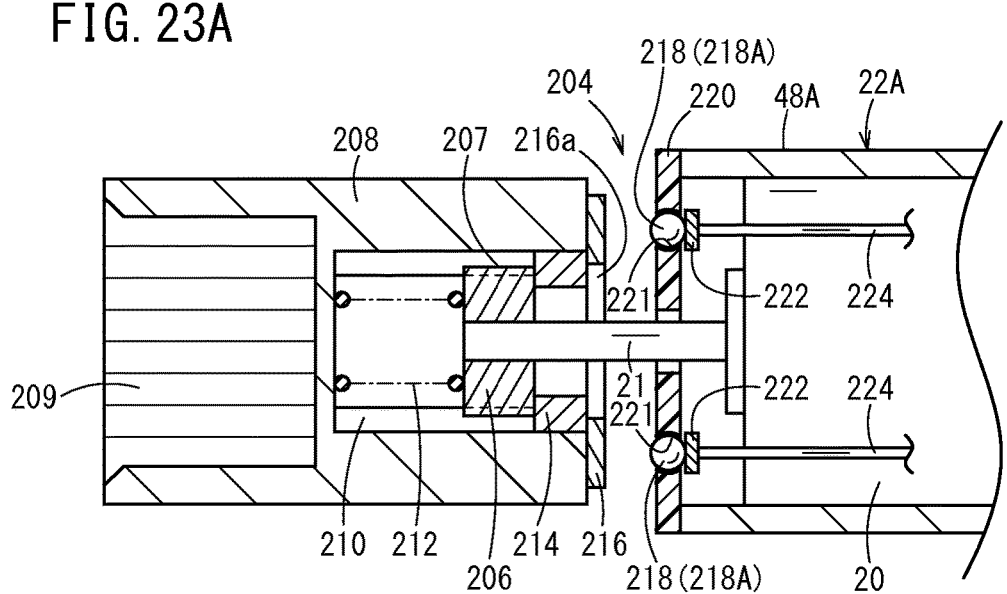
FIG. 23A is a view showing a detection mechanism.
Figure 23B:
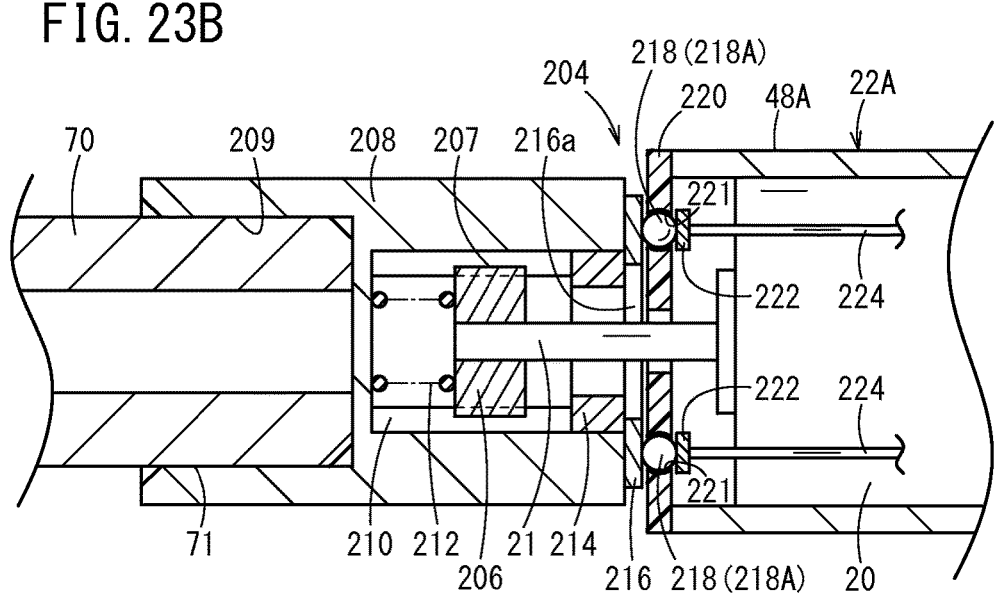
FIG. 23B is a view for describing actions of the detection mechanism.

Instead of a configuration in which attachment of the drive unit 22 to the handle 14 is detected by the handle-side terminal members 82b, 82d (FIG. 7A) and the unit-side terminal members 84b, 84d (FIG. 8) coming into contact, a detection mechanism 204 shown in FIGS. 23A and 23B may be adopted.

As shown in FIG. 23A, an engagement part 206 is fixed to an output shaft 21 of the motor 20. On an outer circumferential portion of the engagement part 206, one engagement projection 207 or a plurality of engagement projections 207 are disposed at predetermined intervals in the circumferential direction. The engagement projection or projections 207 engage with one or a plurality of engagement grooves 210 provided on an inner circumferential part of a proximal end side portion of a drive coupling 208 (drive member). The engagement grooves 210 extend in the axial direction of the drive coupling 208. More specifically, the engagement part 206 and the drive coupling 208 are spline-fitted together. The drive coupling 208 includes plural teeth 209, which are capable of meshing with the driven coupling 70 that is provided on the handle 14. The respective teeth 209, in the same manner as the respective teeth 51 in the drive coupling 50 shown in FIG. 6, may have tooth-end portions that narrow in width toward the distal end direction, or may not have such tooth-end portions (the width thereof may be constant).

The drive coupling 208 is capable of sliding with respect to the engagement part 206. By an engagement action between the engagement projections 207 and the engagement grooves 210, a rotary drive force is transmitted from the engagement part 206 to the drive coupling 208. More specifically, accompanying rotation of the output shaft 21 of the motor 20, the engagement part 206 and the drive coupling 208 are rotated together integrally. Instead of the engagement projections 207 on the engagement part 206, engagement grooves may be provided, and instead of the engagement grooves 210 on the inner circumferential portion of the drive coupling 208, engagement projections may be provided. With such a configuration as well, the drive coupling 208 and the engagement part 206 are spline-fitted together.

A biasing member 212 (a coil spring in the present illustrated example) is disposed between the engagement part 206 and the drive coupling 208. The biasing member 212 of the illustrated example is arranged on an inner side of the drive coupling 208. The biasing member 212 applies an elastic biasing force at all times to the drive coupling 208 in the distal end direction. In the drive coupling 208, an engagement member 214 that engages with the engagement part 206 is disposed on a more proximal side than the engagement part 206. The biasing member 212 may also be constituted from a coil spring, a plate spring, or another elastic body.

A short circuiting ring 216 made up from an electrically conductive material, e.g., a metal or the like, is disposed on a proximal end surface of the drive coupling 208. The output shaft 21 is inserted through the interior of the drive coupling 208 via a hole 216a in the short circuiting ring 216.

A drive unit 22A is capable of being attached and detached with respect to the handle 14, and similar to the drive unit 22 shown in FIG. 1, etc., the drive unit 22A is capable of being connected to the controller 36 through the cable 54. In a housing 48A of the drive unit 22A, at a location corresponding to the short circuiting ring 216, two contact members 218 made from a conductive material are provided. The two contact members 218 of the present illustrated example are constituted by balls 218A. The balls 218A are arranged in retaining holes 221 provided in ball retaining members 220 constituted from an insulating material (for example, a resin or the like). The balls 218A are retained rollably by the ball retaining members 220.

In the interior of the housing 48A, two conductive members 222 made from an electrically conductive material, e.g., a metal or the like, abut respectively against the two balls 218A. Lead wires 224 are connected respectively to the two conductive members 222. The respective lead wires 224 are connected through the cable 54 (see FIG. 1) to the controller 36.

In the detection mechanism 204, which is constructed as described above, in a state in which the drive unit 22A is not attached to the handle 14, as shown in FIG. 23A, the drive coupling 208 is retained in an advanced position by the elastic force of the biasing member 212. Consequently, the short circuiting ring 216 and the two balls 218A (contact members 218) are not in contact, and in the controller 36, attachment of the drive unit 22A with respect to the handle 14 is not detected.

On the other hand, in a state in which the drive unit 22A is attached to the handle 14, as shown in FIG. 23B, the drive coupling 208 is pressed rearwardly by the driven coupling 70. At this time, the drive coupling 208 is moved and retracted in opposition to the elastic force of the biasing member 212, and the short circuiting ring 216 and the two balls 218A are placed in contact. As a result, the two balls 218A are electrically connected via the short circuiting ring 216, and in the controller 36, attachment of the drive unit 22A with respect to the handle 14 is detected.

In the condition shown in FIG. 23B, together with the drive coupling 208 being driven rotatably by the motor 20 through the engagement part 206, the short circuiting ring 216 also is rotated. At this time, although the short circuiting ring 216 and the two balls 218A remain in contact, the balls 218A, which are retained in the ball retaining members 220, are capable of rolling in the retaining holes 221 together with rotation of the short circuiting ring 216. Therefore, in a state in which the short circuiting ring 216 and the contact members 218 are in contact, a large increase in rolling resistance of the drive coupling 208 due to rotation of the drive coupling 208 can effectively be suppressed. Further, the contact members 218 are not limited to the balls 218A. More specifically, the contact members 218 need not necessarily be members that are capable of rolling.

Although certain preferred embodiments of the present invention have been shown and described in detail above, it should be understood that various changes and modifications may be made to the embodiments without departing from the scope of the invention as set forth in the appended claims.

What is claimed is:

1. A medical manipulator comprising:
a handle;
a shaft that is extended from the handle;
a distal end working unit capable of operating with respect to the shaft, the distal end working unit having two jaws; and
a drive source for operating the distal end working unit;
wherein:
a first portion, which includes the distal end working unit and the shaft and on which a driven coupling is disposed, and a second portion, which includes the drive source and on which a drive coupling that is driven by the drive source is disposed, are capable of being attached and detached;
in a state in which the first portion and the second portion are connected, the drive coupling and the driven coupling are fitted together, so that a driving force of the drive source is transmitted to the distal end working unit to open and close the jaws; and
the drive coupling having a proximal end adjacent to the drive source;
the drive coupling having a distal end opposite the proximal end;
the drive coupling having a rotational axis;
a first tooth-end portion extends radially inward from an inner wall of the drive coupling, the first tooth-end portion becomes narrower in a direction parallel to the rotational axis toward the distal end of the drive coupling:
the first tooth-end portion having a height defined by a radial distance from the inner wall of the drive coupling to an apex of the first tooth-end portion, the height decreasing toward the distal end of the drive coupling;
the distal end of the drive coupling having a surface perpendicular to the rotational axis;
the first tooth-end portion terminating at the distal end of the drive coupling with a surface coplanar with the perpendicular surface of the distal end of the drive coupling;
the driven coupling having a proximal end which is inserted into the drive coupling such that the proximal end of the driven coupling is adjacent to the proximal end of the drive coupling; and
the driven coupling tapers such that a diameter of the driven coupling decreases toward the proximal end of the driven coupling.

2. The medical manipulator according to claim 1, wherein:
the first portion comprises a manipulator main body including the handle; and
the second portion comprises the drive unit that is capable of attachment and detachment with respect to the handle.

3. The medical manipulator according to claim 1, wherein on the first tooth-end portion, a curve of a tooth shape forms an involute curve.

4. The medical manipulator according to claim 1, wherein a second tooth-end portion extends radially outward from an outer wall on the driven coupling.

5. The medical manipulator according to claim 1, wherein the distal end working unit is configured to be moveable relative to the shaft.

6. The medical manipulator according to claim 1, wherein the second portion includes a lever configured to operate an end effector on a distal end of the distal end working unit.

7. The medical manipulator according to claim 1, wherein the drive coupling includes a coupling base member and a coupling main body portion, the coupling main body portion having at least one engagement protrusion and the coupling base member having at least one engagement recess, the at least one engagement protrusion smaller than the at least one engagement recess.

8. The medical manipulator according to claim 1, wherein the first tooth-end portion includes a top surface, an end surface, and a tapered portion, the tapered portion defining a section of the tooth-end portion between the top surface and the end surface.

9. A medical manipulator comprising:
a first portion, the first portion including a handle, a shaft extending from the handle, a distal end working unit, and a driven coupling; and
a second portion, the second portion including a drive source configured to operate the distal end working unit, and a drive coupling driven by a drive source;
the first and second portions configured to detach from one another;
wherein when the first and second portions are connected, the drive coupling and the driven coupling are engaged, and a driving force of the drive source is transmitted to the distal end working unit;
the drive coupling having a rotational axis;
the drive coupling includes a first plurality of teeth each having a first tooth-end portion, the first tooth-end portion including a top surface portion, an end surface, and a tapered portion, the tapered portion defining a section of the first tooth-end portion between the top surface portion and the end surface;
the first tooth-end portion extends radially inward from an inner wall of the drive coupling;
each tooth of the first plurality of teeth having a width measured along a circumference of the inner wall of the drive coupling;
the width substantially narrowing in a direction parallel to the rotational axis of the drive coupling and toward the end surface of each tooth;
the first tooth-end portion having a height defined as the radial distance from the inner wall of the drive coupling to the top surface portion, the height decreasing toward the distal end of the drive coupling;
a distal end of the drive coupling having a surface perpendicular to the rotational axis;
the first tooth-end portion terminating at the distal end of the drive coupling with a surface coplanar with the perpendicular surface of the distal end of the drive coupling;
the driven coupling having a proximal end which is inserted into the drive coupling such that the proximal end of the driven coupling is adjacent to the proximal end of the drive coupling; and
the driven coupling tapers such that a diameter of the driven coupling decreases in the direction of the proximal end of the driven coupling.

10. The medical manipulator according to claim 9, wherein the driven coupling includes a second plurality of teeth each having a second tooth-end portion, the second tooth-end portion extends radially outward from an outer wall of the driven coupling.

11. A medical manipulator comprising:
a first portion, the first portion including a handle, a shaft extending from the handle, a distal end working unit, and a driven coupling; and
a second portion, the second portion including a drive source configured to operate the distal end working unit, and a drive coupling driven by a drive source;
the first and second portions configured to detach from one another;
wherein when the first and second portions are connected, the drive coupling and the driven coupling are engaged, and a driving force of the drive source is transmitted to the distal end working unit;
the drive coupling having a rotational axis;
the drive coupling includes a plurality of teeth each having a tooth-end portion, the tooth-end portion including a top surface portion, an end surface, and a tapered portion, the tapered portion defining a section of the tooth-end portion between the top surface portion and the end surface;
the tooth-end portion extends radially inward from an inner wall of the drive coupling;
each tooth of the first plurality of teeth having a width measured along a circumference of the inner wall of the drive coupling;
The width substantially narrowing in a direction parallel to the rotational axis of the drive coupling and toward the end surface of each tooth; and
the drive coupling includes a coupling base member and a coupling main body portion, the coupling main body portion having at least one engagement protrusion and the coupling base member having at least one engagement recess, the at least one engagement protrusion smaller than the at least one engagement recess;
a distal end of the drive coupling disposed opposite the coupling base member, the drive coupling distal end having a surface perpendicular to the rotational axis;
each tooth-end portion terminating with the end surface coplanar with the perpendicular surface of the drive coupling distal end;
each tooth end-portion having a height defined as a radial distance from the inner wall of the drive coupling to the top surface portion of the tooth-end portion, the tooth-end portion height decreasing toward the distal end of the drive coupling;
the driven coupling having a proximal end which is inserted into the drive coupling distal end such that the proximal end of the driven coupling is adjacent to the coupling base member; and
the driven coupling tapers such that a diameter of the driven coupling decreases in the direction toward the proximal end of the driven coupling.

12. The medical manipulator according to claim 11, wherein the drive coupling includes a gap between the at least one engagement protrusion and the at least one engagement recess.

* * * * *